US008322339B2

(12) United States Patent
Gottlib et al.

(10) Patent No.: US 8,322,339 B2
(45) Date of Patent: Dec. 4, 2012

(54) METHOD AND SYSTEM OF DETECTING FAULTS IN A BREATHING ASSISTANCE DEVICE

(75) Inventors: Kelly S. Gottlib, San Ramon, CA (US); Philip K. Snyder, Livermore, CA (US); Michael J. Fullmer, Alameda, CA (US); Charles E. Porges, Orinda, CA (US); Bonny Setzer, Pleasanton, CA (US)

(73) Assignee: Nellcor Puritan Bennett LLC, Boulder, CO (US)

( * ) Notice: Subject to any disclaimer, the term of this patent is extended or adjusted under 35 U.S.C. 154(b) by 1583 days.

(21) Appl. No.: 11/469,677

(22) Filed: Sep. 1, 2006

(65) Prior Publication Data

US 2008/0053441 A1 Mar. 6, 2008

(51) Int. Cl.
*A62B 7/00* (2006.01)
*A61M 16/00* (2006.01)

(52) U.S. Cl. ............... 128/205.23; 128/204.18

(58) Field of Classification Search ............ 128/200.24, 128/202.22, 203.12–203.14, 204.18, 204.21–204.23, 128/204.26, 205.23; 600/529, 538
See application file for complete search history.

(56) References Cited

U.S. PATENT DOCUMENTS

| 3,120,843 | A | 2/1964 | Hyman | 128/202.22 |
|---|---|---|---|---|
| 3,333,584 | A | 8/1967 | Andreasen et al. | 128/202.22 |
| 3,595,228 | A | 7/1971 | Simon et al. | 128/202.22 |
| 3,741,208 | A | 6/1973 | Jonsson et al. | 128/204.21 |
| 3,811,400 | A | 5/1974 | Smilg | 116/70 |
| 3,831,595 | A | 8/1974 | Valenta et al. | 128/202.22 |
| 3,848,591 | A | 11/1974 | Smythe et al. | 128/204.23 |
| 3,867,934 | A | 2/1975 | Ollivier | 128/202.22 |
| 3,877,467 | A | 4/1975 | Plicchi | 128/202.22 |
| 3,916,888 | A | 11/1975 | Buck et al. | 128/204.21 |
| 4,096,858 | A | 6/1978 | Eyrick et al. | 128/205.16 |
| 4,155,357 | A | 5/1979 | Dahl | 128/202.22 |
| 4,176,617 | A | 12/1979 | Pilipski | 116/70 |
| 4,286,589 | A | 9/1981 | Thompson | 128/202.22 |
| 4,287,886 | A | 9/1981 | Thompson | 128/202.22 |
| 4,302,640 | A | 11/1981 | Vicenzi et al. | 200/81 R |
| 4,318,399 | A | 3/1982 | Berndtsson | 128/204.23 |
| 4,550,726 | A | 11/1985 | McEwen | 128/202.22 |
| 4,674,492 | A | 6/1987 | Niemeyer | 128/202.22 |
| 4,765,326 | A | 8/1988 | Pieper | 128/202.22 |

(Continued)

FOREIGN PATENT DOCUMENTS

AU 79077194 A 6/1995

(Continued)

OTHER PUBLICATIONS

International Search Report with Written Opinion, Feb. 14, 2008, 16 pages, PCT/US20071077195.

(Continued)

*Primary Examiner* — Justine Yu
*Assistant Examiner* — Rachel Young

(57) ABSTRACT

A breathing assistance system with functionality for detecting the existence of a fault condition may include a pressure detector, a flow detector and a fault detection system. The pressure detector may take pressure measurements, each measurement including a measurement of a gas flow rate in the breathing assistance system. The flow detector may take flow rate measurements, each flow rate measurement including a measurement of has flow rate in the breathing assistance system. The fault detection system may process the pressure measurements and/or flow rate measurements to determine the existence of a fault condition associated with the breathing assistance system.

29 Claims, 9 Drawing Sheets

U.S. PATENT DOCUMENTS

| | | | |
|---|---|---|---|
| 4,766,894 A | 8/1988 | Legrand et al. | 128/204.21 |
| 4,825,802 A | 5/1989 | Le Bec | 116/70 |
| 4,870,393 A | 9/1989 | Snuttjer et al. | 340/611 |
| 4,883,051 A | 11/1989 | Westenskow et al. | 128/204.21 |
| 4,899,740 A | 2/1990 | Napolitano | 128/202.22 |
| 4,971,049 A | 11/1990 | Rotariu | |
| 4,990,894 A | 2/1991 | Loescher et al. | 340/573 |
| 5,035,239 A | 7/1991 | Edwards | 128/205.23 |
| 5,042,470 A | 8/1991 | Kanesaka | 128/202.22 |
| 5,057,822 A | 10/1991 | Hoffman | 340/611 |
| 5,097,826 A | 3/1992 | Gray et al. | 128/204.18 |
| 5,148,802 A | 9/1992 | Sanders | |
| 5,165,397 A | 11/1992 | Arp | 128/204.21 |
| 5,303,699 A | 4/1994 | Bonassa et al. | 128/204.21 |
| 5,313,937 A | 5/1994 | Zdrojkowski | 128/202.22 |
| 5,320,092 A | 6/1994 | Ryder | 128/202.22 |
| 5,503,146 A * | 4/1996 | Froehlich et al. | 128/204.23 |
| 5,517,983 A | 5/1996 | Deighan et al. | 128/204.23 |
| 5,537,997 A | 7/1996 | Mechlenburg et al. | 128/204.23 |
| 5,577,496 A | 11/1996 | Blackwood et al. | 128/201.25 |
| 5,603,315 A | 2/1997 | Sasso, Jr. | 128/204.18 |
| 5,626,129 A | 5/1997 | Klimm et al. | 128/202.22 |
| 5,640,149 A | 6/1997 | Campbell | 340/626 |
| 5,645,054 A | 7/1997 | Cotner | |
| 5,715,812 A | 2/1998 | Deighan et al. | 128/204.23 |
| 5,720,709 A | 2/1998 | Schnall | 600/538 |
| 5,735,267 A * | 4/1998 | Tobia | 128/204.21 |
| 5,740,796 A | 4/1998 | Skog | 128/204.23 |
| 5,873,361 A | 2/1999 | Hakala | 128/204.23 |
| 5,881,717 A | 3/1999 | Isaza | 128/202.22 |
| 5,901,704 A | 5/1999 | Estes et al. | 128/204.23 |
| 5,950,621 A | 9/1999 | Klockseth et al. | 128/204.26 |
| 5,970,975 A | 10/1999 | Estes et al. | 128/204.23 |
| 6,067,022 A | 5/2000 | Laswick et al. | 340/626 |
| 6,085,747 A | 7/2000 | Axe | |
| 6,123,074 A | 9/2000 | Hete et al. | 128/205.11 |
| 6,209,579 B1 | 4/2001 | Rowden et al. | 137/557 |
| 6,269,811 B1 | 8/2001 | Duff et al. | 128/204.21 |
| 6,360,741 B2 | 3/2002 | Truschel | 128/202.22 |
| 6,386,196 B1 | 5/2002 | Culton | 128/205.23 |
| 6,392,555 B1 | 5/2002 | Most, Jr. | 340/664 |
| 6,591,834 B1 | 7/2003 | Colla et al. | 128/204.21 |
| 6,615,828 B1 | 9/2003 | Petherbridge | 128/200.28 |
| 6,629,527 B1 | 10/2003 | Estes et al. | 128/204.18 |
| 6,668,824 B1 | 12/2003 | Isaza et al. | 128/202.22 |
| 6,745,768 B2 | 6/2004 | Colla et al. | 128/204.21 |
| 6,840,240 B1 | 1/2005 | Berthon-Jones et al. | 128/204.21 |
| 6,844,691 B2 | 1/2005 | Chiang et al. | 318/268 |
| 7,040,317 B2 | 5/2006 | Colla et al. | 128/204.18 |
| RE39,225 E | 8/2006 | Isaza et al. | 128/202.22 |
| 2003/0062045 A1 | 4/2003 | Woodring et al. | 128/204.18 |
| 2003/0066529 A1 | 4/2003 | Truschel | |
| 2004/0050387 A1 | 3/2004 | Younes | |
| 2004/0226561 A1 | 11/2004 | Colla et al. | 128/204.21 |
| 2005/0087187 A1 | 4/2005 | Berthon-Jones et al. | 128/200.24 |
| 2005/0087190 A1 * | 4/2005 | Jafari et al. | 128/204.21 |
| 2005/0263155 A1 | 12/2005 | Gossweiler | 128/205.23 |
| 2006/0070624 A1 * | 4/2006 | Kane et al. | 128/204.23 |
| 2006/0107953 A1 * | 5/2006 | Truschel et al. | 128/204.18 |

FOREIGN PATENT DOCUMENTS

| | | |
|---|---|---|
| EP | 0 459 647 | 12/1991 |
| EP | 0 099 743 | 2/1994 |
| EP | 0621056 A1 | 10/1994 |
| EP | 0661071 B1 | 7/1995 |
| EP | 0 742 027 | 11/1996 |
| EP | 0774233 A1 | 5/1997 |
| GB | 2215216 B1 | 9/1989 |
| WO | 9215355 A1 | 9/1992 |
| WO | 9603174 A1 | 2/1996 |
| WO | 9933508 A1 | 7/1999 |
| WO | 0027457 A1 | 5/2000 |

OTHER PUBLICATIONS

Pediatric-Adult Star 1500 Ventilator, Markting Brochure, Infrasonics, Inc. Star Products; 7 pages, 1996.

* cited by examiner

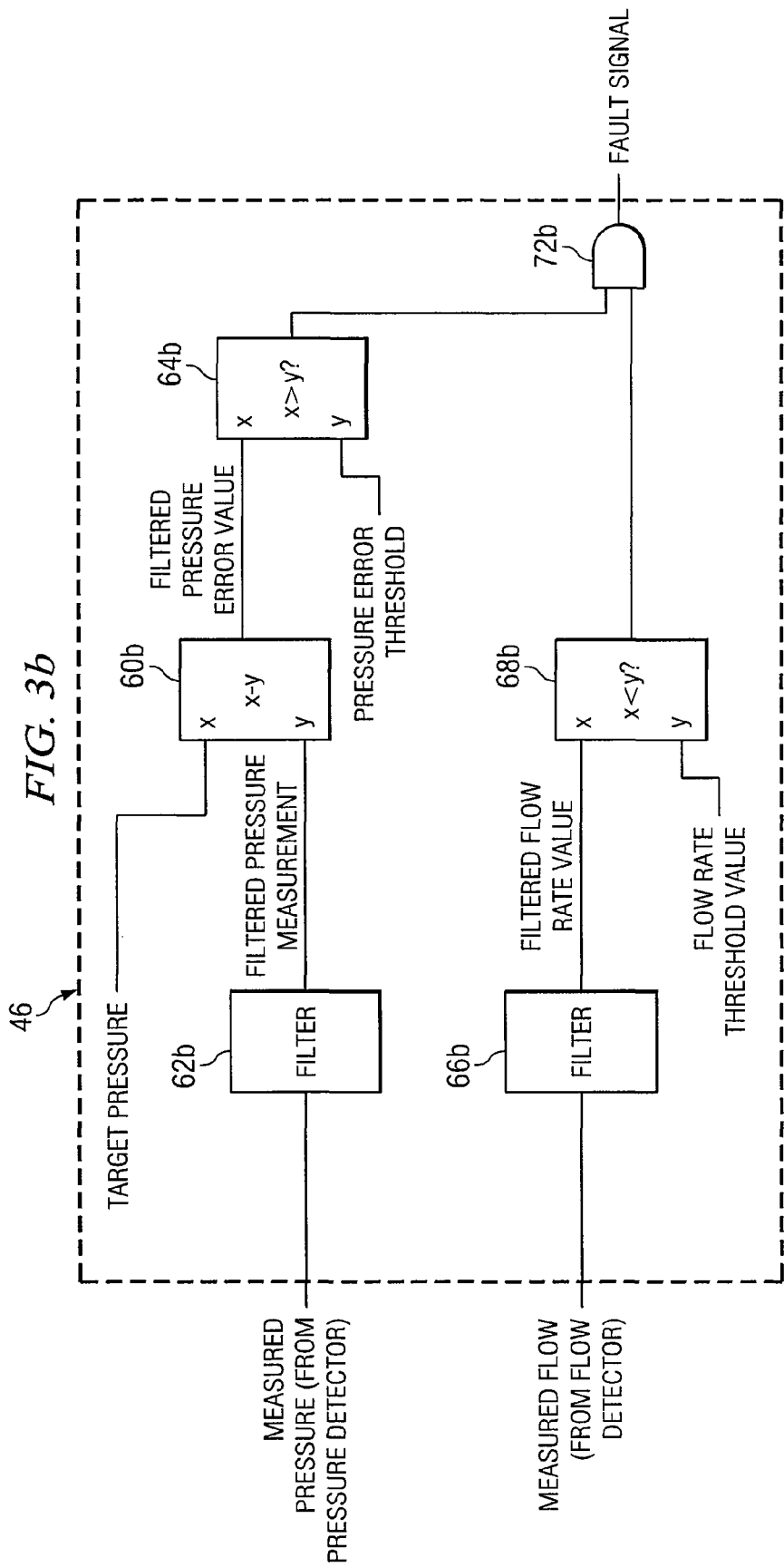

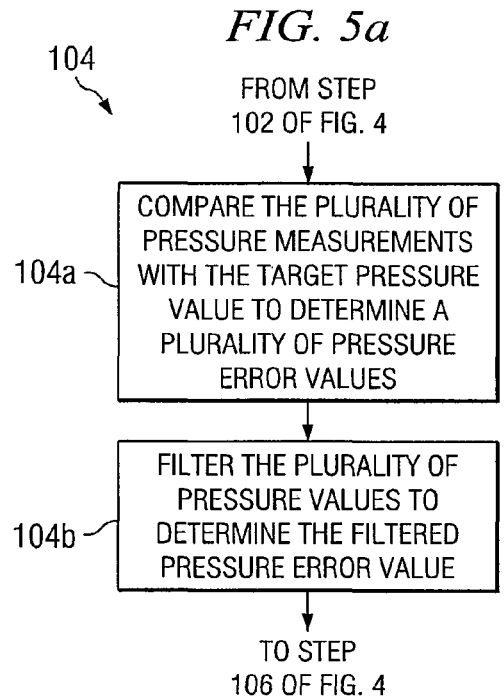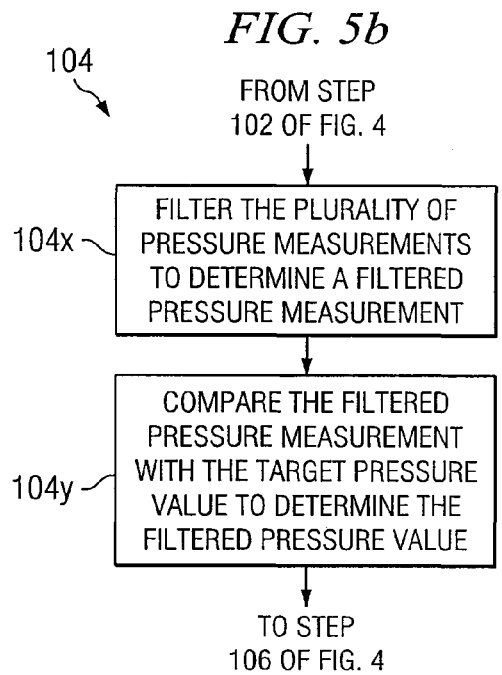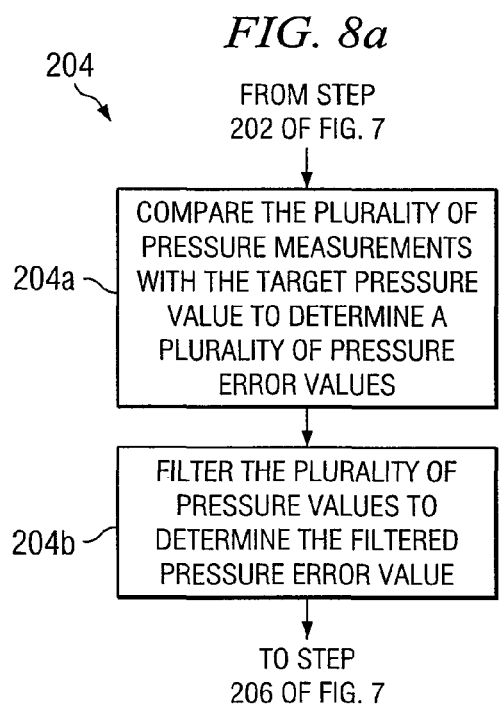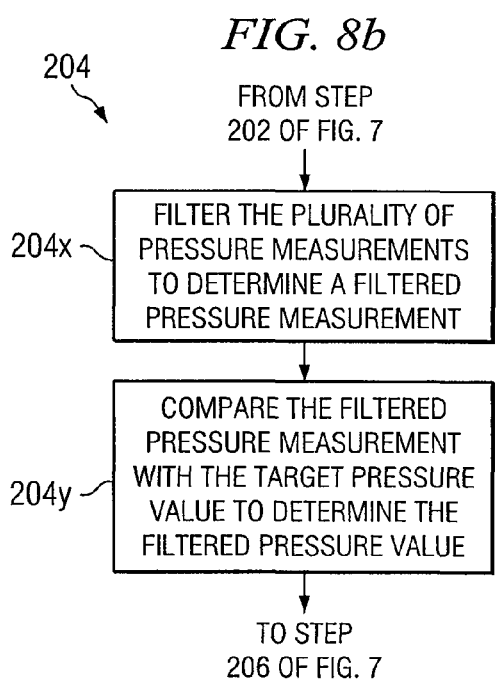

METHOD AND SYSTEM OF DETECTING FAULTS IN A BREATHING ASSISTANCE DEVICE

TECHNICAL FIELD

The present disclosure relates generally to breathing assistance devices, e.g., systems and methods for detecting faults in a breathing assistance device.

BACKGROUND

A breathing assistance device typically delivers pressurized breathing gas to a patient via tubing called a "patient interface" or a "breathing circuit." The breathing gas typically includes air and/or one or more gasses (e.g., oxygen mixed with the air). The breathing gas delivered to the patient from the breathing assistance device may be humidified and/or heated in the breathing circuit before being delivered to the patient. The breathing assistance device typically increases the pressure in the breathing circuit so that the breathing gas is pushed into the lungs for inspiration, and reduces the pressure in the breathing circuit so that gases in the lungs can be expired and vented to the atmosphere. Typically, one or more breathing assistance device parameters may be determined and/or adjusted prior to and/or during operation, e.g., the mode of ventilation (e.g., CMV (controlled mandatory ventilation), SIMV (synchronized intermittent mandatory ventilation), CPAP (constant positive airway pressure), or bi-level CPAP); the patient's tidal volume (the volume of gas inspired with each breath); the respiratory rate (the number of breaths per minute (BPM)); and/or the $O_2$ concentration, flow rate, airway pressure, and/or minute volume (the volume inspired and expired in one minute) of breathing gas delivered to the patient.

Operational faults may occur in breathing assistance devices from time to time. For example, a fault within a source of pressurized gas flow (or a "gas flow source") associated with a breathing assistance system, e.g., a blower, compressor, or a piston-based device, may occur. While such a fault may inhibit operation of the gas flow source, electrical current to the proper gas flow source may continue, potentially causing the gas flow source to overheat, cause injury to the patient or cause a fire (possibly leading to expensive damage to the breathing assistance device), or even cause an explosion (possibly leading to injury to a patient or other person). As a further example of a potential fault, a portion of a patient interface (e.g., a patient mask, nasal pillows, or an air tube) associated with a breathing assistance device may become disconnected from the patient and/or the breathing assistance device. In some instances, such a disconnection may cause a control circuit associated with the breathing assistance device to erroneously detect that the airway pressure being delivered to the patient is too low, and the control circuit may increase the pressure and/or flow of gas provided to the patient, which may, e.g., cause mechanical stresses within the breathing assistance device, and/or waste of electrical power. In addition, other faults may occur within a breathing assistance system that may be detected using some or all of the methods and systems herein disclosed.

SUMMARY

In accordance with one embodiment of the present disclosure, a method of detecting a fault condition in a breathing assistance system is provided. A plurality of pressure measurements, each pressure measurement comprising a measurement of a gas pressure in the breathing assistance system, may be received over time. Based at least on the plurality of pressure measurements and a target pressure value, a filtered pressure error value may be determined, the determination including filtering a plurality of values. A plurality of flow rate measurements, each flow rate measurement comprising a measurement of a gas flow rate in the breathing assistance system, may be received over time. The plurality of flow rate measurements may be filtered to determine a filtered flow rate value. Based on a least the filtered pressure error value and the filtered flow rate value, the existence of a fault condition may be determined.

In accordance with another embodiment of the present disclosure, a breathing assistance system operable to detect a fault condition may include a pressure detector, a flow detector, and a fault detection system. The pressure detector may be operable to take pressure measurements, each pressure measurement comprising a measurement of a gas pressure in the breathing assistance system. The flow detector may be operable to take flow rate measurements, each flow rate measurement comprising a measurement of a gas flow rate in the breathing assistance system. The fault detection system may be communicatively coupled to the pressure detector and the flow detector, and may be operable to: (a) receive a plurality of pressure measurements taken over time from the pressure detector; (b) determine a filtered pressure error value based at least on the plurality of pressure measurements and a target pressure value, the determination including filtering a plurality of values; (c) receive a plurality of flow rate measurements taken over time, each flow rate measurement comprising a measurement of a gas flow rate in the breathing assistance system; (d) filter the plurality of flow rate measurements to determine a filtered flow rate value; and (e) determine the existence of a fault condition based at least on the filtered pressure error value and the filtered flow rate value.

In accordance with yet another embodiment of the present disclosure, a method of detecting a fault condition in a breathing assistance system is provided. A plurality of pressure measurements, each pressure measurement comprising a measurement of a gas pressure in the breathing assistance system, may be received over time. A filtered pressure measurement may be determined by processing the plurality of pressure measurements to reduce the effects of the outlying pressure measurements, and a pressure error value may be determined by comparing the filtered pressure measurement with a target pressure value. The existence of a fault condition may be determined based at least on the determined pressure error value.

In accordance with still another embodiment of the present disclosure, a method of detecting a fault condition in a breathing assistance system is provided. A plurality of pressure measurements, each pressure measurement comprising a measurement of a gas pressure in the breathing assistance system, may be received over time. A plurality of pressure error values may be determined by comparing the plurality of pressure measurements with a target pressure value, and a filtered pressure error value may be determined by processing the plurality of pressure error values to reduce the effects of outlying pressure error values. The existence of a fault condition may be determined based at least on the filtered pressure error value.

BRIEF DESCRIPTION OF THE DRAWINGS

A more complete understanding of the present embodiments may be acquired by referring to the following description taken in conjunction with the accompanying drawings, in which like reference numbers indicate like features, and wherein:

FIGS. 3A and 3B each illustrate an example of a fault detection system for use in the breathing assistance systems shown in FIGS. 1 and 2, in accordance with certain embodiments of the disclosure;

FIGS. 5A and 5B each illustrate an example method of determining a filtered pressure error value in the method shown in FIG. 4, in accordance with certain embodiments of the disclosure;

FIGS. 8A and 8B each illustrate an example method of determining a filtered pressure error value in the method shown in FIGS. 7A and 7B, in accordance with certain embodiments of the disclosure.

DETAILED DESCRIPTION

Embodiments of the disclosure may be understood by reference to FIGS. 1 through 8B, wherein like numbers are used to indicate like and corresponding parts.

Figure 1:
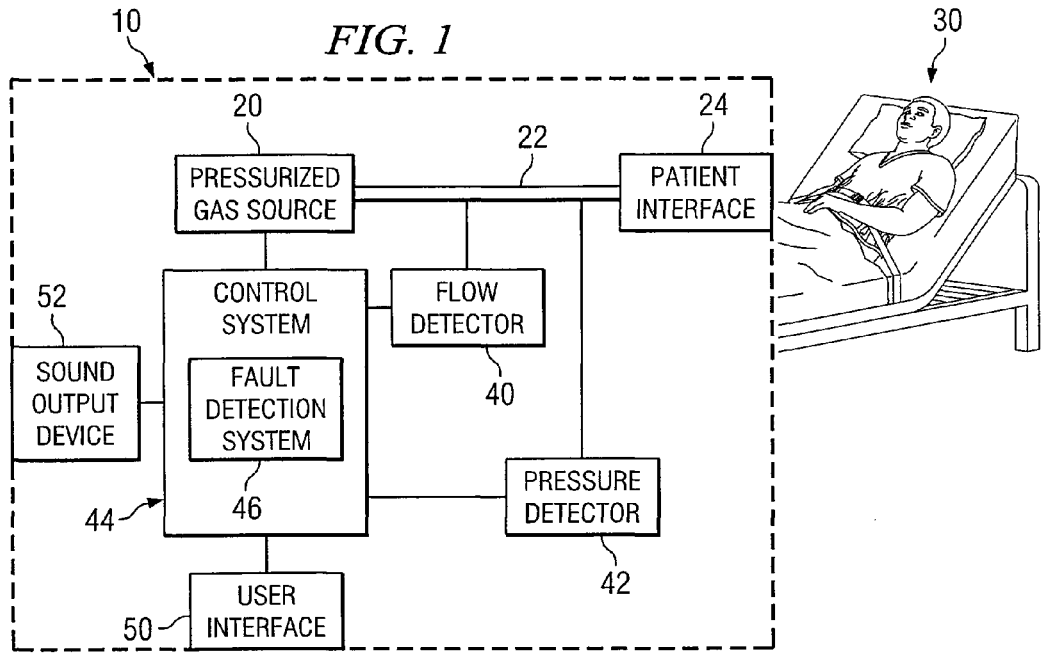
FIG. 1 illustrates a breathing system having fault condition detection functionality in accordance with one embodiment of the disclosure.

FIG. 1 illustrates a breathing assistance system 10 having fault condition detection functionality in accordance with one embodiment of the disclosure. In general, the fault condition detection functionality may detect one or more faults produced by the operation of breathing assistance system 10. Generally, a fault produced in breathing assistance system 10 may be dynamically detected and analyzed to determine whether a fault has occurred, and in some embodiments, determine the type of fault occurring. In some embodiments, the fault condition detection functionality may detect faults associated with a source of pressurized gas flow (referred to herein as a "gas flow source") associated with breathing assistance system 10. In addition or in other embodiments, the fault condition detection functionality may detect faults associated with the disconnection of a connection system associated with breathing assistance system 10. In addition or in other embodiments, the fault condition detection functionality may utilize pressure and flow rate measurements taken within breathing assistance system 10 in order to determine whether a fault condition has occurred.

As used herein, the term "fault" may refer to any generally undesirable condition that may be caused by or associated with the operation of breathing assistance system 10, such as an error, shutdown, lock-up, malfunction or other fault associated with a gas flow source of breathing assistance system 10, or the decoupling of a patient interface from a patient and/or from system 10, for example. The term "patient" may refer to any person or animal that may receive breathing assistance from system 10, regardless of the medical status, official patient status, physical location, or any other characteristic of the person. Thus, for example, patients may include persons under official medical care (e.g., hospital patients), persons not under official medical care, persons receiving care at a medical care facility, persons receiving home care, etc.

As shown in FIG. 1, breathing assistance system 10 may include a gas flow source 20, a connection system 22, a patient interface 24, a flow detector 40, a pressure detector 42, a control system 44, and a user interface 50. Gas flow source 20 may comprise any system or device suitable for generating and/or delivering pressurized gas (e.g., air and/or oxygen or one or more other supplemental gasses) toward a patient 30, including without limitation, a blower, a compressor, a piston-based device, one or more pressurized gas tanks, one or more gas lines (e.g., from a wall or other source), or any combination thereof. Further, in embodiments with one or more gas lines supplying gas to breathing assistance system 10, gas flow source 20 may comprise one or more valves (e.g. solenoid or other valves) configured to control the volume and/or pressure of gas delivered towards patient 30. Disabling of gas flow source 20 may include, e.g., switching off or turning off gas flow source 20 or breathing assistance system 10 or disconnecting the energy source or power source from gas flow source 20. For example, where gas flow source 20 is a blower, disabling may include switching off or turning off blower 21 or disconnecting the energy source or power source from gas flow source 21. As another example, where gas flow source 20 includes one or more valves (e.g. solenoid or other valves) controlling the supply of gas to patient 30, disabling may include closing or opening valves, or disconnecting the energy source or power source of such valves.

Connection system 22 may include any system or device suitable for delivering pressurized gas generated by gas flow source 20 towards patient 30, e.g., a connection system and/or other conduits and connection devices. In some embodiments, connection system 22 may include a proximal pressure line operable to detect gas pressure near patient 30 in connection system 22 or patient interface 24. Patient interface 24 may include any system or device suitable for further delivering pressurized gas delivered by connection system 22 to patient 30, e.g., a nasal or face mask, nasal pillows, and/or a tube (e.g., an endotracheal tube, a tracheostomy tube and/or other tracheal tube).

Flow detector 40 may generally be operable to detect the flow rate of gas flowing through one or more conduits of system 10, e.g., the flow rate produced by gas flow source 20 or the flow rate of gas delivered to patient 30. Flow detector 40 may include any number of sensors operable to detect flow rate of a gas and/or any device operable to convert a detected flow rate into electrical signals or otherwise sense flow rate. Flow detector 40 may be placed at any suitable location and in any suitable orientation for sensing flow rate of a gas within breathing assistance system 10. For example, flow detector 40 may be placed within connection system 22, or near gas flow source 20, an air intake port, and/or an air outlet port.

Pressure detector 42 may generally be operable to detect a pressure of gas within one or more conduits of breathing assistance system 10 by gas flow source 20 and/or the pressure of gas delivered to patient 30. Pressure detector 42 may include any number of sensors operable to detect gas pressure and/or any suitable device operable to convert a detected pressure into electrical signals or otherwise sense pressure. Pressure detector 42 may be placed at any suitable location and in any suitable orientation for sensing gas pressure within breathing assistance system 10. For example, pressure detector 42 may be placed within connection system 22, or near gas flow source 20, an air intake port, and/or an air outlet port.

User interface 50 may include any suitable device or devices allowing a user to interface with breathing assistance system 10, e.g., to input desired performance parameters that may be communicated to control system 44 to control the operation of gas flow source 20 and/or other components of breathing assistance system 10. For example, user interface 50 may allow a user to input one or more of the following performance parameters: the age, weight, tidal volume capacity, respiratory rate, inhale sensitivity, exhale sensitivity, circuit leak, rise time, alarm settings, delay, ramp, starting pressure, inhalation:exhalation (I:E) ratio, and/or other characteristics of patient 30, a desired gas flow rate to patient 30, desired gas pressure or pressures to patient 30, a selected ventilation program, and/or various control (e.g., on/off control or algorithm selection) for the fault detection functionality.

Control system 44 may generally be operable to process various inputs, e.g., input from user interface 50, ventilation programs stored in memory, and/or feedback from flow detector 40, pressure detector 42, or other variables sensed or otherwise detected by other sensors associated with breathing assistance system 10, and to regulate the operation of gas flow source 20 or other components of breathing assistance system 10 based on such various inputs. Control system 44 may include any suitable system or device for controlling the operation of breathing assistance system 10, including, e.g., a microcontroller, a digital signal processor (DSP), an application specific integrated controller (ASIC), electrically-programmable read-only memory (EPROM), or a field-programmable gate array (FPGA). In some embodiments, control system 44 may include software and/or other executable code for analyzing input signals received from user interface 50 and/or feedback from flow detector 40, pressure detector 42, or other variables sensed or otherwise detected by other sensors associated with breathing assistance system 10 to generate control signals for regulating the operation of breathing assistance system 10. Such software may include any suitable algorithms, logic and/or instructions for processing signals in breathing assistance system 10, and may be stored in any suitable data storage media. In some embodiments, for example those in which control system 44 comprises an FPGA, the functionality of such software may be programmed into the FPGA rather than provided as separate software.

In some embodiments, control system 44 controls the operation of gas flow source 20. For example, where gas flow source 20 comprises a motorized blower control system 44 may control the operation (e.g., the motor speed and on/off control) of the blower. In addition, control system 44 may generate sound signals to be broadcast by breathing assistance system 10, such as user feedback (e.g., instructions or other words) or other sounds regarding the operation of breathing assistance system 10. For example, control system 44 may monitor the operation of breathing assistance system 10 and, when appropriate, generate alarm signals (e.g., a siren, buzzer, or words) to be broadcast by a sound output device 52.

Control system 44 may also comprise a fault detection system 46. Fault detection system 46 may generally be operable to process various inputs, e.g., input from user interface 50, and/or feedback from flow detector 40, pressure detector 42, or other variables sensed or otherwise detected by other sensors associated with breathing assistance system 10, and to determine the existence or absence of a fault condition. For example, control system 44 may monitor the operation of breathing assistance system 10 (e.g., the detected flow rate and/or pressure measurements from flow detector 40 and pressure detector 42, respectively), and when appropriate, (a) generate alarm signals to be broadcast by sound output device 52 and/or (b) disable operation of gas flow source 20 or other components of breathing assistance system 10. In some embodiments, fault detection system 46 includes software and/or executable code for analyzing input signals received from user interface 50 and/or feedback from flow detector 40, pressure detector 42 or other variables sensed or otherwise detected by other sensors associated with breathing assistance system 10 to generate control signals for regulating the operation of breathing assistance system 10. Such software may include any suitable algorithms, logic and/or instructions for processing signals in breathing assistance system 10, and may be stored in any suitable data storage media.

Thus, control system 44 may provide, without limitation, any or all of the following functions: (a) controlling the operation of gas flow source 20, (b) monitoring the operation of ventilator 10 and/or generating alarm signals to be broadcast by sound output device 52, (c) generating user feedback signals to be broadcast by sound output device 52, and/or (d) processing signals received by control system 44 to generate (1) alarm signals to be broadcast by sound output device 52 and/or (2) control signals to disable operation of gas flow source 20 or other components of breathing assistance system 10.

Sound output device 52 may generally be operable to output sound signals generated by control system 44, for example, user feedback and/or alarms. Sound output device 52 may include a speaker and an audio driver operable to control the speaker. Sound input device 52 may comprise any suitable type of speaker, such as a cone or ribbon-based loudspeaker, for example. Sound output device 52 may comprise any audio driver or other program or device that controls the operation of a speaker. The audio driver may act as a translator between control system 44 and sound output device 52. In some embodiments, sound output device 52 may simultaneously broadcast multiple sound signals.

Figure 2:
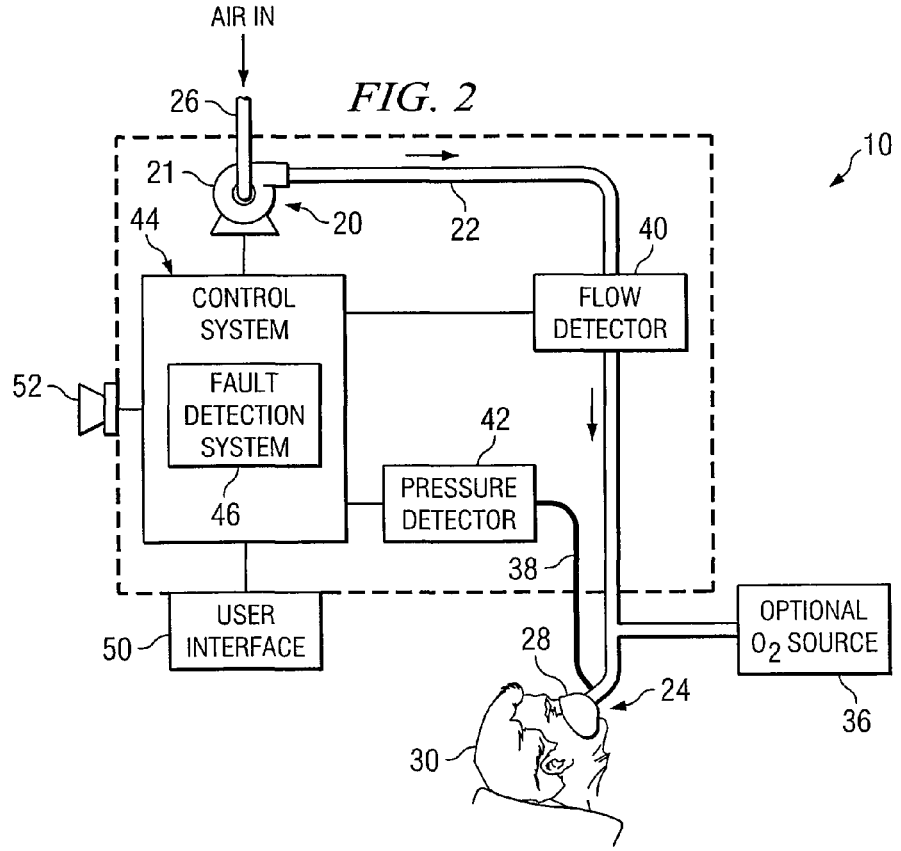
FIG. 2 illustrates a more detailed view of an example breathing assistance system having fault condition detection functionality in accordance with one embodiment of the disclosure.

FIG. 2 illustrates a more detailed view of an example breathing assistance system 10 having fault condition detection functionality in accordance with one embodiment of the disclosure. Breathing assistance system 10 may include a gas flow source 20 comprising a motorized blower 21, an air inlet channel 26, a connection system 22, a flow detector 40, a pressure detector 42, a control system 44 comprising a fault detection system 46, a user interface 50, a sound output device 52, a pressure line 38, an optional oxygen source 36, and/or a patient interface 24 comprising a mask 28. It should be understood that breathing assistance system 10 may also include any other suitable components for providing fault condition detection functions. In some embodiments, breathing assistance system 10 may be a compact, portable breathing assistance system, such as a breathing assistance system for home use. In other embodiments, breathing assistance system 10 may be a larger, more complex breathing assistance system, such as for use in a hospital.

In the embodiment depicted in FIG. 2, gas flow source 20 comprises a blower 21 (e.g., a blower having an impeller driven by a motor). Blower 21 may generally be operable to receive atmospheric air from air inlet channel 26, pressurize the air, and deliver the pressurized air through connection system 22.

As discussed above, connection system 22 may include any system or device suitable for delivering pressurized gas generated by blower 21 towards patient 30, e.g., a patient circuit. In some embodiments, connection system 22 may include a proximal pressure line operable to detect gas pressure near patient 30 in connection system 22 or patient interface 24. Patient interface 24 may include any system or device suitable for further delivering pressurized gas delivered by connection system 22 to patient 30. In this example embodiment, patient interface 24 comprises a mask 28, e.g., a nasal mask or a face mask.

Also as discussed above, flow detector 40 may generally be operable to detect flow rate, for example, the flow rate of pressurized gas generated by blower 21 and delivered to patient 30. Flow detector 40 may include any number of sensors operable to detect flow rate of a gas and/or any other device operable to convert a detected flow rate into electrical signals or otherwise sense flow rate. Pressure detector 42 may generally be operable to detect a pressure of gas within one or more conduits of breathing assistance system 10. Furthermore, pressure detector 42 may include any number of sensors operable to detect pressure of a gas and/or any other suitable device operable to convert a detected pressure into electrical signals or otherwise sense pressure. In the embodiment depicted in FIG. 2, breathing assistance system 10 may include a pressure line 38 fluidically coupled to pressure detector 42 and operable to communicate a detected pressure (e.g., near blower 21, within connection system 22, within mask 28, and/or near patient 30) to pressure detector 42.

Also as noted above, user interface 50 may include any suitable device or devices allowing a user to interface with breathing assistance system 10, e.g., to input desired performance parameters that may be communicated to control system 44 to control the operation of blower 21 and/or other components of breathing assistance system 10.

As discussed above, control system 44 may generally be operable to process various inputs, e.g., input from user interface 50, ventilation programs stored in memory, and/or feedback from flow detector 40, pressure detector 42 or other variables sensed or otherwise detected by other sensors associated with breathing assistance system 10, and to regulate the operation of blower 21 or other components of breathing assistance system 10 based on such various inputs. In some embodiments, control system 44 controls the operation of blower 21. For example, control system 44 may control the operation (e.g., the motor speed and on/off control) of blower 21. Furthermore, control system 44 may generate other sound signals to be broadcast breathing assistance system 10, e.g., user feedback (e.g., instructions or other words) and/or other sounds regarding the operation of breathing assistance system 10. For example, control system 44 may monitor the operation of breathing assistance system 10 and, when appropriate, generate alarm signals (e.g., a siren, buzzer, or words) to be broadcast by sound output device 52.

Control system 44 may comprise fault detection system 46. As discussed above, fault detection system 46 may generally be operable to process various inputs, e.g., input from user interface 50, and/or feedback from flow detector 40, pressure detector 42 or other variables sensed or otherwise detected by other sensors associated with breathing assistance system 10, and to determine the existence or absence of a fault condition. For example, control system 44 may monitor the operation of breathing assistance system 10 (e.g., the detected flow rate and/or pressure measurements from flow detector 40 and pressure detector 42, respectively), and when appropriate, (a) generate alarm signals (e.g., a siren, buzzer, or words) to be broadcast by sound output device 52 and/or (b) disable operation of blower 21 or other components of breathing assistance system 10.

Breathing assistance system 10 may also include optional oxygen source 36. Optional oxygen source 36 may generally be operable to provide a supply of oxygen to patient 30 supplemental to the pressurized gas provided by blower 21. Optional oxygen source 36 may be fluidically coupled to connection system 22 and may comprise a blower, a compressor, a piston-based device, one or more pressurized gas tanks, or one or more gas lines (e.g., from a wall or other source). Optional oxygen source 36 may be placed at any suitable location and in any suitable orientation for providing a supplemental flow of oxygen within breathing assistance system 10. For example, optional oxygen may be physically connected to connection system 22 near patient interface 24 or blower 21, or may be physically connected to air inlet channel 26.

Figure 3A:
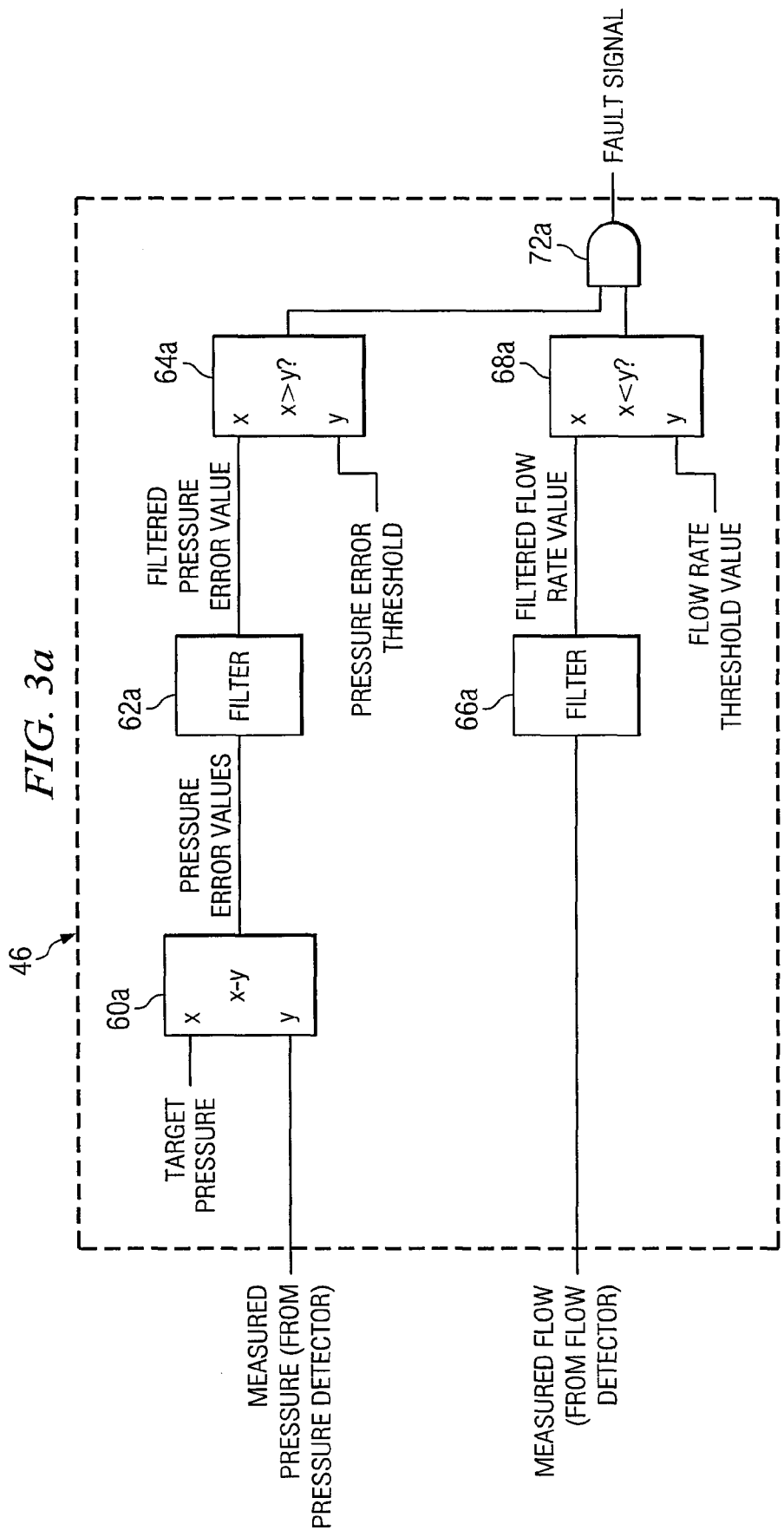

FIGS. 3A and 3B each illustrate an example of fault detection system 46 for use in the breathing assistance systems 10 shown in FIG. 1 and FIG. 2, in accordance with certain embodiments of this disclosure. As depicted in FIGS. 3A and 3B, fault detection system 46 may be operable to: (a) receive a plurality of pressure measurements taken over time by pressure detector 42; (b) determine a filtered pressure error value based at least on the plurality of pressure measurements and a target pressure value, the determination including filtering a plurality of values; (c) receive a plurality of flow rate measurements taken over time by flow detector 40, each flow rate measurement comprising a measurement of gas flow rate in breathing assistance system 10; (d) filter the plurality of flow rate measurements to determine a filtered flow rate value; and (e) determine the existence of a fault condition based at least on the filtered pressure error value and the filtered flow rate value.

As shown in FIG. 3A, fault detection system 46 may include a subtractor 60a, filters 62a and 66A, comparators 64a and 68A, and an AND gate 72a. Subtractor 60a may generally be operable to compare each of a plurality of pressure measurements detected over time by pressure detector 42 with a target pressure value (which may be set or selected by a user and/or by control system 44) to determine a plurality of pressure error values, each representing a difference between the target pressure value and the current detected pressure. In some embodiments, if the difference between the target pressure value and the current detected pressure is a positive value, subtractor 60a may determine the corresponding pressure error value to be equal to the difference, and may determine the corresponding pressure error value to be zero (0) if the difference is a negative value. In the depicted embodiment, subtractor 60a may determine each pressure error value by subtracting each measured pressure value from the target pressure value. Filter 62a may generally be operable to filter the plurality of pressure error values, determined by subtractor 60a to determine a filtered pressure error value. Comparator 64a may generally be operable to compare the filtered pressure error value determined by filter 62a to a pressure error threshold value and generate an output based on the comparison. In the depicted embodiment, comparator 64a may generate an output of TRUE or logic 1 if the filtered pressure error value is greater than the pressure error threshold value, and may otherwise generate an output of FALSE or logic 0.

Filter 66A may generally be operable to filter the plurality of flow rate measurements detected over time by flow detector 40 to determine a filtered flow rate value. Comparator 68A may generally be operable to compare the filtered flow rate value to a flow rate threshold value and generate an output based on the comparison. In the depicted embodiment, comparator 68A may generate an output of TRUE or logic 1 if the filtered flow rate value is less than the flow rate threshold value, and may otherwise generate an output of FALSE or logic 0. AND gate 72*a* may generally be operable to output a signal indicating whether or not a fault condition has been detected by fault detection system 46 by performing a logical AND of the outputs of comparators 64*a* and 68A. If the depicted embodiment, AND gate 72*a* generates an output of TRUE or logic 1 to denote a fault condition if each of comparators 64*a* and 68A generate an output of TRUE or logic 1; otherwise AND gate 72*a* generates an output of FALSE or logic 0 to denote no fault condition.

As shown in FIG. 3B, fault detection system 46 may include a subtractor 60*b*, filters 62*b* and 66B, comparators 64*b* and 68B, and an AND gate 72*b*. Filter 62*b* may generally be operable to filter a plurality of pressure measurements detected over time by pressure detector 42 to determine a filtered pressure measurement. Subtractor 60*b* may generally be operable to compare the filtered pressure measurement determined by filter 62*b* with a target pressure value (which may be set or selected by a user and/or by control system 44) to determine a filtered pressure error value, representing the difference between the target pressure value and the filtered pressure measurement. In some embodiments, subtractor 60*b* may output the difference between the target pressure value and the filtered pressure measurement if such difference is a positive value, and may output a value of zero (0) if the difference is a negative value.

Comparator 64*b* may generally be operable to compare the filtered pressure error value determined by subtractor 60*b* to a pressure error threshold and generate an output based on the comparison. In the depicted embodiment, comparator 64*b* may generate an output of TRUE or logic 1 if the filtered pressure error value is greater than the pressure error threshold, and may otherwise generate an output of FALSE or logic 0.

Filter 66B may generally be operable to filter a plurality of flow rate measurements detected over time by flow detector 40 to determine a filtered flow rate value. Comparator 68B may generally be operable to compare the filtered flow rate value determined by filter 66B to a flow rate threshold value and generate an output based on the comparison. In the depicted embodiment, comparator 68B may generate an output of TRUE or logic 1 if the filtered flow rate value is less than the flow rate threshold value, and may otherwise generate an output of FALSE or logic 0. AND gate 72*b* may generally be operable to output a signal indicating whether or not a fault condition has been detected by fault detection system 46 by performing a logical AND of the outputs of comparators 64*b* and 68B. If the depicted embodiment, AND gate 72*b* generates an output of TRUE or logic 1 to denote a fault condition if each of comparators 64*b* and 68B generate an output of TRUE or logic 1; otherwise AND gate 72*b* generates an output of FALSE or logic 0 to denote no fault condition.

In some embodiments, the generation of a fault signal by fault detection system 46 to denote a fault condition may indicate a fault associated with gas flow source 20. For example, in the embodiment depicted in FIG. 2, a fault condition generated by detecting a filtered pressure error value above the pressure error threshold value and detecting a filtered flow rate value below the flow rate threshold value may indicate a malfunction or other fault associated with blower 21, e.g., where blower 21 has unexpectedly ceased to provide pressurized gas or has become stalled. In such situations, it may be desirable to alert a human of the fault condition and/or disable operation of blower 21 (e.g. by removing the source of energy of the blower) to prevent damage to breathing assistance system 10 or other deleterious effects, e.g., a fire or injury to the patient. Thus, in some embodiments, control system 44 may, in response to a determination by fault detection system 46 that a fault condition exists, cause breathing assistance system 10 to generate an alert detectable by a human. Such an alert may include, e.g., an audible alert generated by sound output device 52 and/or a visual alert displayed on user interface 50. In addition or alternatively control system 44 may disable the operation of blower 21 if fault detection system 46 determines that a fault condition exists.

As noted above, in some embodiments, the target pressure value may be selected by a user of breathing assistance system 10, e.g., a patient or a caregiver. Such selection of the target pressure value can be made by means of any suitable system or device, for example, user interface 50. In some embodiments or situations, the target pressure value may be elected directly by a user, e.g., by using user interface 50. In other embodiments or situations, the target pressure value may be calculated by control system 44 based on one or more other parameters, e.g., gas flow parameters selected by a user or the selected ventilation mode (e.g., if a CPAP mode is selected, control system 44 may calculate the target pressure value based on experimentally determined optimum values for such mode; or a user may select a desired flow rate and control system 44 may calculate a target pressure value based at least on such desired flow rate).

In some embodiments, the flow rate threshold value and/or the pressure error threshold value are set to provide desired levels of sensitivity to the fault detection functionality disclosed herein. For example, flow rate threshold value and/or the pressure error threshold may be set in order to minimize or eliminate determination of false positives or false negatives of fault conditions in breathing assistance system 10. In some embodiments, the flow rate threshold value and/or the pressure error threshold value may be selected based on experimentation, e.g., experimentation by a manufacturer or a caregiver.

In some embodiments, at least one of (a) the flow rate threshold value and (b) the pressure error threshold value may be selected by a user of breathing assistance system 10, e.g., a developer, manufacturer, or caregiver. Such selection of the flow rate threshold value and/or pressure error threshold value can be made by means of any suitable system or device, for example, user interface 50. In other embodiments, the flow rate threshold value and/or the pressure error threshold value may be determined automatically or otherwise based on the age, weight, tidal volume capacity, respiratory rate, inhale sensitivity, exhale sensitivity, circuit leak, rise time, alarm settings, delay, ramp, starting pressure, inhalation:exhalation (I:E) ratio, and/or other characteristics of the patient, a desired gas flow rate to the patient, desired gas pressure or pressures to the patient, a selected ventilation program, and/or various control (e.g., on/off control or algorithm selection) for the fault detection functionality, and may be automatically adjusted over time based on such parameter(s). In a particular embodiment, the pressure error threshold may be based at least on the target pressure value (e.g., the pressure error threshold may be automatically set or adjusted to some specified percentage of the target pressure value).

In some embodiments, the pressure error threshold value may range from about 1 cm $H_2O$ to about 3 cm $H_2O$. In a particular embodiment, the pressure error threshold may be about 2 cm $H_2O$. In some embodiments, the flow rate threshold value may range from about 5 LPM to about 15 LPM. In a particular embodiment, the flow rate threshold may be about 10 LPM.

In embodiments in which there are significant pressure fluctuations over time (e.g. during bi-level CPAP therapy), the embodiment depicted in FIG. 3A may be preferable over the embodiment depicted in FIG. 3B because of the pressure fluctuations associated with bi-level therapy.

Each of filters 62a, 62b, 66A and 66B may comprise any suitable system or device for filtering a plurality of values to reduce the effects of outlying values (e.g., outlying pressure measurements, flow rate measurements, or pressure error values) or other transient faults associated with detecting pressure or flow rate in breathing assistance system 10, that might, without such filtering, cause false positives and/or false negatives of a fault condition. Such outlying measurements or transient faults may occur as a result of, e.g., a patient cough, the patient's natural breath cycle, or electromagnetic interference that may momentarily cause large transient pressure detection faults or low transient flow rate detection faults. Filters 62a, 62b, 66A and 66B may comprise, without limitation, one or more averagers and/or low-pass filters, such as infinite impulse response (IIR) filters, for example.

Each of subtractors 60a and 60b, filters 62a, 62b, 66A and 66B, comparators 64a, 64b, 68A and 68B, and AND gates 72a and 72b may comprise any suitable system or device for carrying out the functionality of each such component as discussed above. For example, in some embodiments, each component of fault detection system 46 may be implemented on one or more integrated circuits, including without limitation a microcontroller, a digital signal processor (DSP), an application specific integrated controller (ASIC), electrically-programmable read-only memory (EPROM) or a field-programmable gate array (FPGA). In some embodiments, each of subtractors 60a and 60b, filters 62a, 62b, 66A and 66B, comparators 64a, 64b, 68A and 68B, and AND gates 72a and 72b may be contained on or within multiple integrated circuits. In another embodiment, two or more of subtractors 60a and 60b, filters 62a, 62b, 66A and 66B, comparators 64a, 64b, 68A and 68B, and AND gates 72a and 72b may be contained on the same integrated circuit.

In one embodiment, one or more of subtractors 60a and 60b, filters 62a, 62b, 66A and 66B, comparators 64a, 64b, 68A and 68B, and AND gates 72a and 72b may include software and/or executable code for analyzing input signals by the respective components to generate appropriate output signals as discussed above. In some embodiments, each of subtractors 60a and 60b, filters 62a, 62b, 66A and 66B, comparators 64a, 64b, 68A and 68B, and AND gates 72a and 72b may be implemented in different software programs or routines. In another embodiment, two or more of subtractors 60a and 60b, filters 62a, 62b, 66A and 66B, comparators 64a, 64b, 68A and 68B, and AND gates 72a and 72b may be implemented within the same software program or routine.

Figure 4:
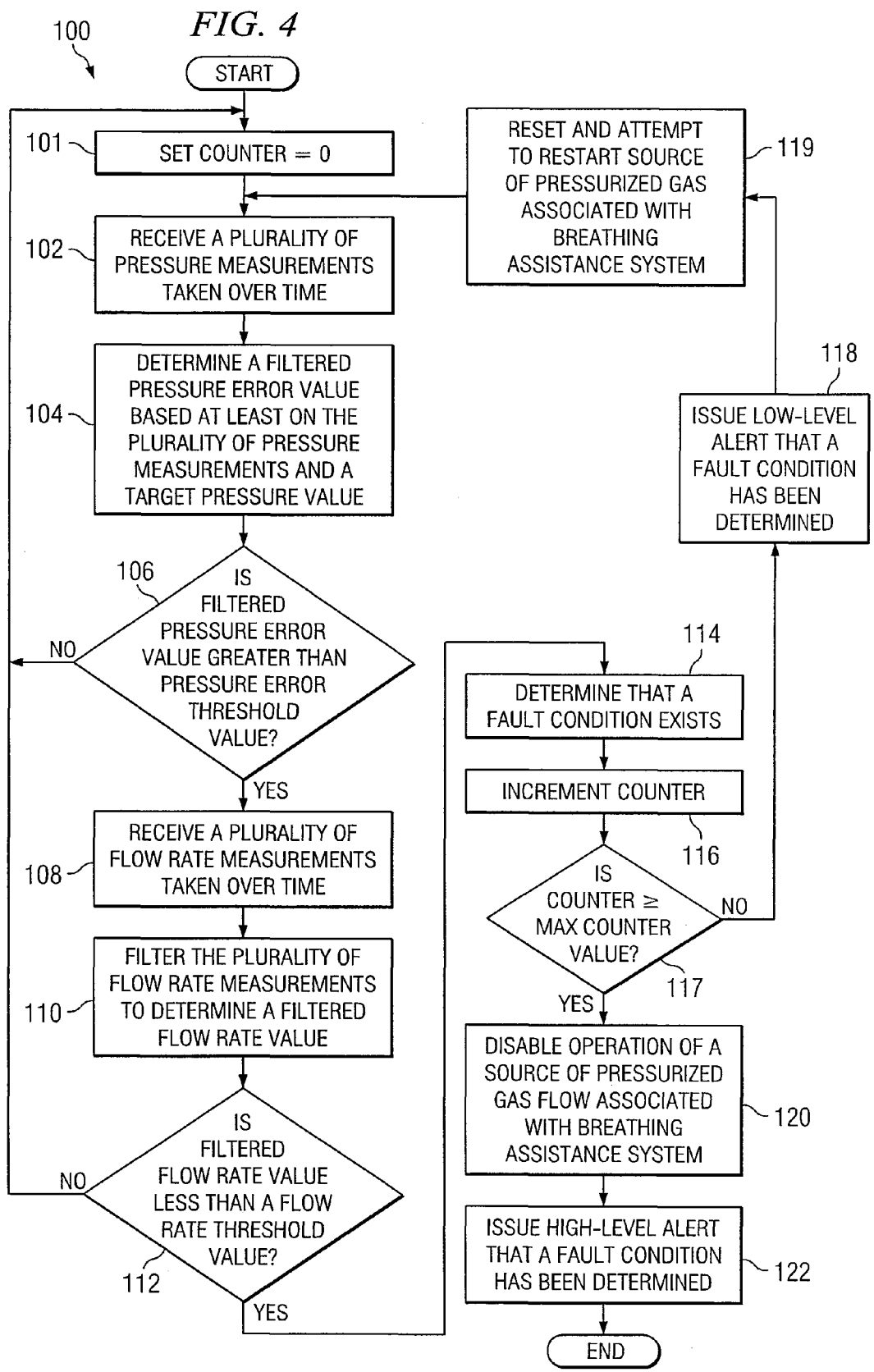
FIG. 4 illustrates an example method of detecting a fault condition in the breathing assistance systems shown in FIGS. 1 and 2, in accordance with one embodiment of the disclosure.

FIG. 4 illustrates a method 100 of detecting a fault condition in a breathing assistance system such as the breathing assistance systems 10 shown in FIG. 1 or 2, in accordance with one embodiment of the disclosure. FIGS. 5A and 5B each illustrate a method of determining a filtered pressure error value in method 100 shown in FIG. 4, in accordance with certain embodiments of the disclosure.

Turning to FIG. 4, at step 101, a counter may be set to zero (0). The counter may be implemented using any suitable method and/or system for implementing a counter. At step 102, fault detection system 46 may receive a plurality of pressure measurements taken over time by pressure detector 42. At step 104, fault detection system 46 may determine a filtered pressure error value based at least on the plurality of received pressure measurements and a target pressure value.

In one embodiment of method 100, step 104 may be implemented by fault detection system 46 as shown in FIG. 5A. At step 104a, subtractor 60a of fault detection system 46 may compare each of the plurality of pressure measurements received from pressure detector 42 with the target pressure value to determine a plurality of pressure error values. Each determined pressure error value may be equal to the target pressure value minus a measured pressure from pressure detector 42. At step 104b, filter 62a of fault detection system 46 may filter the plurality of pressure error values to determine a filtered pressure error value.

In another embodiment of method 100, step 104 may be implemented by fault detection system 46 as shown in FIG. 5B. At step 104x, filter 62b of fault detection system 46 may filter the plurality of pressure measurements received from pressure detector 42 to determine a filtered pressure measurement. At step 104y, subtractor 60b may compare the filtered pressure measurement with the target pressure value to determine a filtered pressure error value. The filtered pressure error value may equal the target pressure value minus the filtered pressure measurement.

Referring again to FIG. 4, at step 106, comparator 64a or 64b of fault detection system 46 may compare the filtered pressure error value with a pressure error threshold value. If the filtered pressure error value is not greater than the pressure error threshold value, method 100 may return to step 101. However, if the filtered pressure error value is greater than the pressure error threshold value, method 100 may proceed to step 108.

At step 108, fault detection system 46 may receive a plurality of flow rate measurements taken over time by flow rate detector 40. At step 110, filter 66A or 66B of fault detection system 46 may filter the plurality of flow rate measurements to determine a filtered flow rate value. At step 112, comparator 68A or 68B of fault detection system 46 may compare the filtered flow rate value with a flow rate threshold value. If the filtered flow rate value is not greater than the flow rate threshold value, method 100 may return to step 101. However, if the filtered flow rate value is greater than the flow rate threshold value, method 100 may proceed to step 114.

At step 114, fault detection system 46 may, based at least on (a) the comparison of the filtered pressure error value to the pressure error threshold value at step 106, and (b) the comparison of the filtered flow rate value with the flow rate threshold value at step 112, determine that a fault condition exists. At step 116, the counter set to zero in step 101 may be incremented by one (1). Thus, the value of the counter at any given time may represent the number of consecutive instances that fault detection system 46, using method 100, has determined the existence of a fault condition. At step 117, the value of the counter may be compared against a predetermined counter value threshold. If the counter value is less than the predetermined counter value threshold, method 100 may proceed to step 118 to communicate an alarm, reset and attempt to restart gas flow source 20, and check whether the fault still exists, as explained below. If the counter value is greater than or equal to the predetermined counter value threshold, method 100 may proceed to step 120 to disable the energy source of gas flow source 20, as explained below.

At step 118, control system 44, fault detection system 46, or another component of breathing assistance system 10 may cause sound output device 52 or user interface 50 to communicate an alert detectable to a human, e.g., an audible sound and/or a visual signal, in response to the determination of the fault condition at step 114. At step 119, control system 44, fault detection system 46, or another component of breathing assistance system 10 may reset and attempt to restart gas flow source 20. After the execution of step 119, method 100 may return to step 102 to check whether the fault condition still exists.

At step 120, control system 44, fault detection system 46, or another component of breathing assistance system 10 may disable operation of gas flow source 20 (e.g., blower 21) in response to the determination at step 117 that the counter value is greater than or equal to the predetermined counter value threshold. At step 122, control system 44, fault detection system 46, or another component of breathing assistance system 10 may cause sound output device 52 or user interface 50 to communicate an alert detectable to a human, e.g., an audible sound and/or a visual signal, in response to the determination at step 117 that the counter value is greater than or equal to the predetermined counter value threshold. In some embodiments, the alert communicated at step 122 may be different than the alert communicated at step 118. In some embodiments, the alert communicated at step 122 may indicate that it is a higher-level alert or higher-priority alert than the alert communicated at step 118. Thus, control system 44, fault detection system 46, or another component of breathing assistance system 10 may disable operation of gas flow source 20 (e.g., blower 21) and/or communicate an alert if fault detection system 46 has determined a fault to exist in a number of consecutive instances equal to the predetermined counter value threshold. In some embodiments, the predetermined counter value threshold may be set to provide desired levels of sensitivity to the fault detection functionality disclosed herein. For example, the predetermined counter value threshold may be set in order to minimize or eliminate determination of false positives or false negatives of fault conditions in breathing assistance system 10. As another example, in situations in which the incidence of false positives or false negatives is not a concern, the predetermined counter value threshold may be set to one (1), or the steps of method 100 relating to the counter discussed above may be eliminated. In some embodiments the predetermined counter value threshold may be selected based on experimentation, e.g., experimentation by a manufacturer or a caregiver. After the execution of step 122, method 100 may end.

Although FIGS. 4, 5A and 5B set forth a series of steps that may be utilized to determine the existence of a fault condition in breathing assistance device 10, it is understood that a fault condition may be detected without utilizing one or more of the steps described above or further utilizing one or more steps not described above. Furthermore, although FIGS. 4, 5A and 5B set forth a particular order of steps that may be utilized to determine the existence of a fault condition in breathing assistance device 10, it is understood that a fault condition may be detected in accordance with the present disclosure using any order of steps discussed above.

Figure 6A:
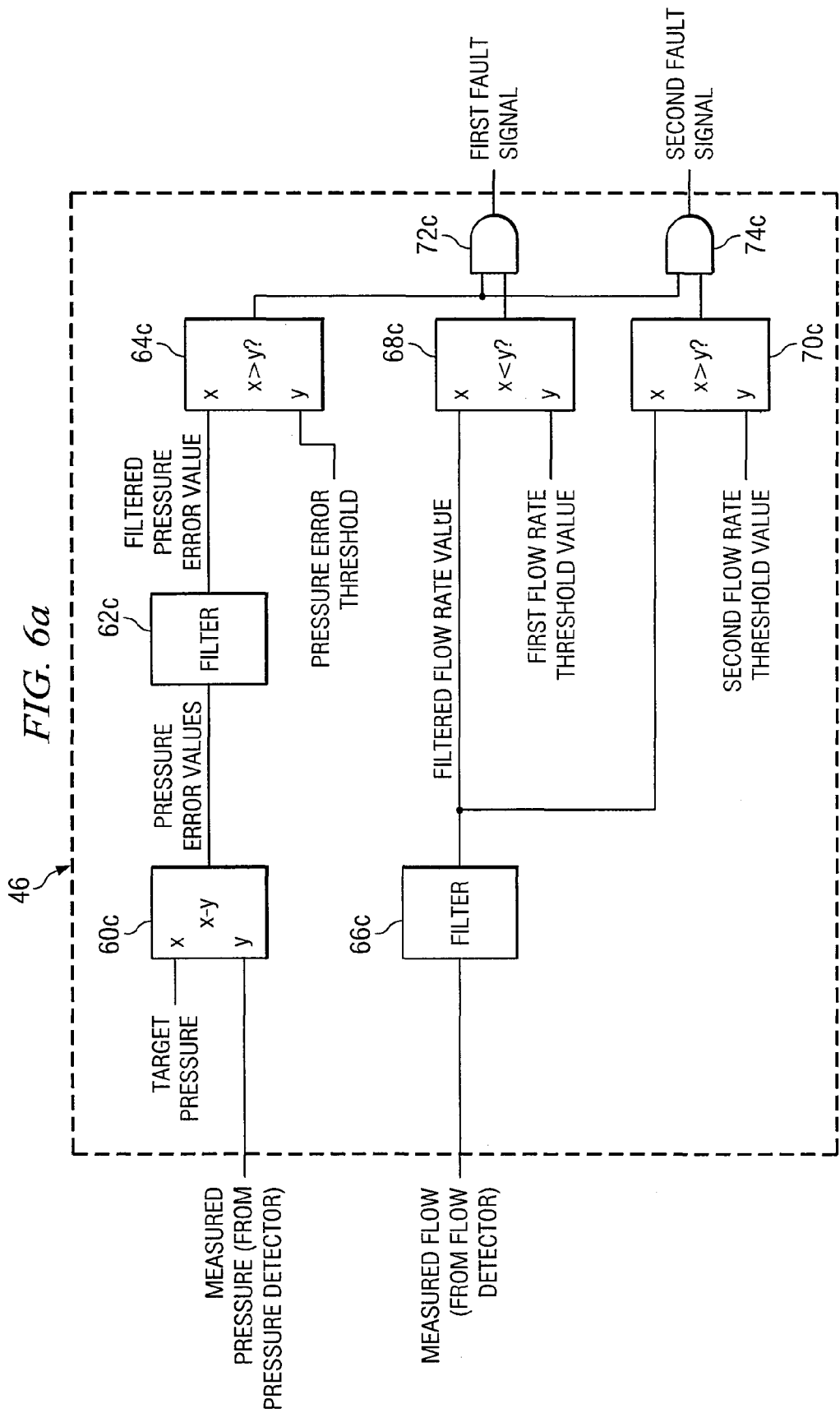
FIGS. 6A and 6B each illustrate an example of a fault detection system for use in the breathing assistance systems shown in FIGS. 1 and 2, in accordance with certain embodiments of the disclosure.
Figure 6B:
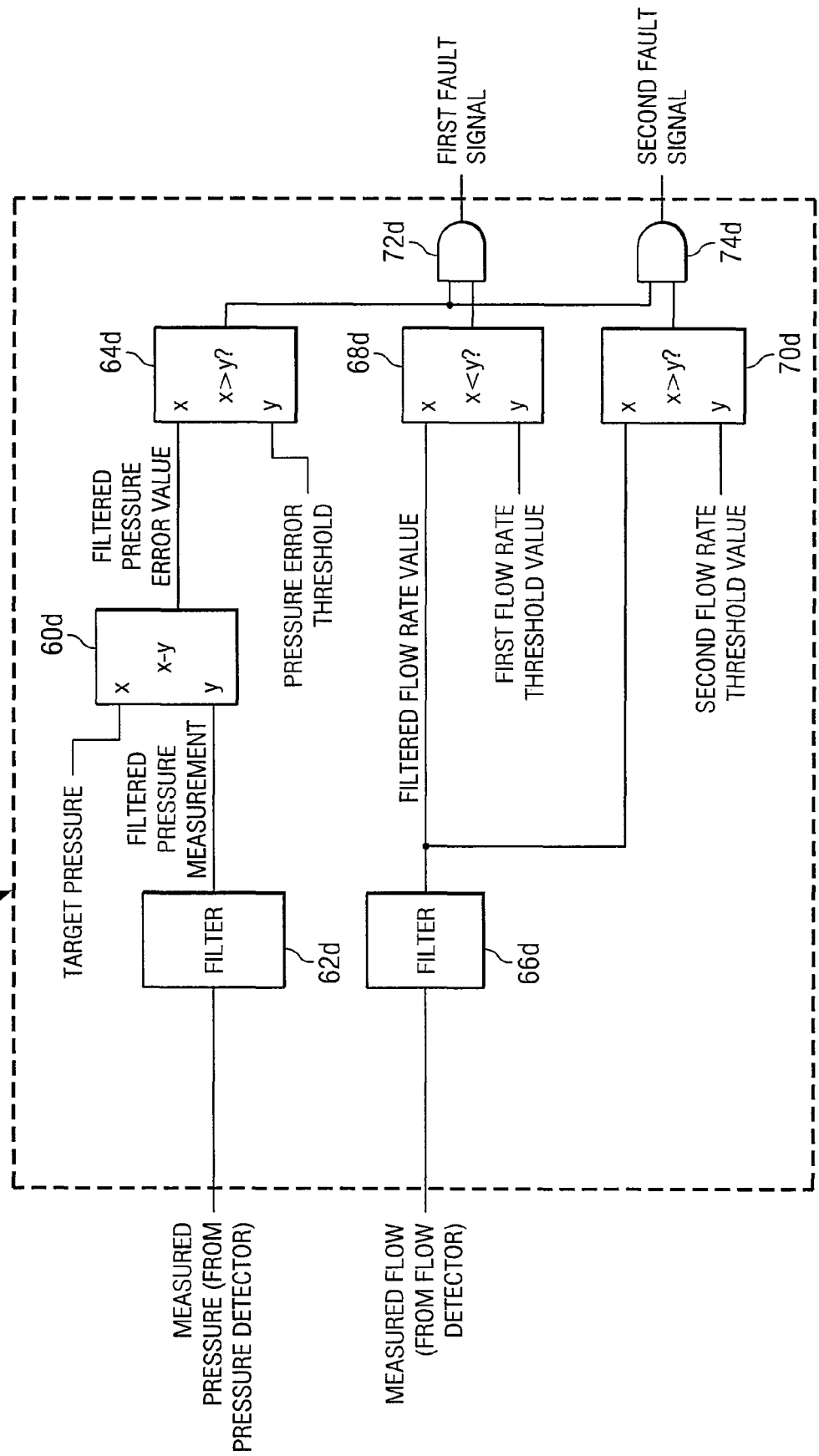

FIGS. 6A and 6B each illustrate an example of a fault detection system 46 for use in a breathing assistance system, such as the breathing assistance systems 10 shown in FIG. 1 or 2, in accordance with certain embodiments of the disclosure. As depicted in FIGS. 6A and 6B, fault detection system 46 may be operable to: (a) receive a plurality of pressure measurements taken over time by pressure detector 42; (b) determine a filtered pressure error value based at least on the plurality of pressure measurements and a target pressure value, the determination including filtering a plurality of values; (c) receive a plurality of flow rate measurements taken over time by flow detector 40, each flow rate measurement comprising a measurement of gas flow rate in breathing assistance system 10; (d) filter the plurality of flow rate measurements to determine a filtered flow rate value; and (e) determine the existence of a fault condition based at least on the filtered pressure error value and the filtered flow rate value.

As shown in FIG. 6A, fault detection system 46 may include a subtractor 60c, filters 62c and 66c, comparators 64c, 68c, and 70c and AND gates 72c and 74c. Subtractor 60c may generally be operable to compare each of a plurality of pressure measurements detected over time by pressure detector 42 with a target pressure value (which may be set or selected by a user and/or by control system 44) to determine a plurality of pressure error values. In the depicted embodiment, each pressure error value may be determined by subtractor 60c by subtracting each measured pressure value from the target pressure value. In some embodiments, if the difference between the target pressure value error value and the current detected pressure is a positive value, subtractor 60c may determine the corresponding pressure error value to be equal to difference, and may determine the corresponding pressure error value to be zero (0) if the difference is a negative value. Filter 62c may generally be operable to filter the plurality of pressure error values determined by subtractor 60c to determine a filtered pressure error value. Comparator 64c may generally be operable to compare the filtered pressure error value determined by filter 62c to a pressure error threshold value and generate an output based on the comparison. In the depicted embodiment, comparator 64c may generate an output of TRUE or logic 1 if the filtered pressure error value is greater than the pressure error threshold value, and may otherwise generate an output of FALSE or logic 0.

Filter 66c may generally be operable to filter a plurality of flow rate measurements detected over time by flow detector 40 to determine a filtered flow rate value. Comparator 68c may generally be operable to compare the filtered flow rate value to a first flow rate threshold value and generate an output based on the comparison. In the depicted embodiment, comparator 68c may generate an output of TRUE or logic 1 if the filtered flow rate value is less than the first flow rate threshold value, and may otherwise generate an output of FALSE or logic 0. Similarly, comparator 70c may generally be operable to compare the filtered flow rate value to a second flow rate threshold value (which may or may not be equal to the first flow rate threshold value) and generate an output based on the comparison. In the depicted embodiment, comparator 70c may generate an output of TRUE or logic 1 if the filtered flow rate value is greater than the second flow rate threshold value, and may otherwise generate an output of FALSE or logic 0.

AND gate 72c may generally be operable to output a first fault signal indicating whether or not a fault condition has been detected by fault detection system 46 by performing a logical AND of the outputs of comparators 64c and 68c. In the depicted embodiment, AND gate 72c generates an output of TRUE or logic 1 to denote a fault condition if each of comparators 64c and 68c generate an output of TRUE or logic 1; otherwise AND gate 72c generates an output of FALSE or logic 0 to denote no fault condition. Similarly, AND gate 74c may generally be operable to output a second fault signal indicating whether or not a fault condition has been detected by fault condition detection system 46 by performing a logical AND of the outputs of comparators 64c and 70c. In the depicted embodiment, AND gate 74c generates an output of TRUE or logic 1 to denote a fault condition if each of comparators 64c and 70c generate an output of TRUE or logic 1; otherwise AND gate 74c generates an output of FALSE or logic 0 to denote no fault condition.

As shown in FIG. 6B, fault detection system 46 may include a subtractor 60d, filters 62d and 66d, comparators 64d, 68d and 70d, and AND gates 72d and 74d. Filter 62d may generally be operable to filter a plurality of pressure measurements detected over time by pressure detector 42 to determine a filtered pressure measurement. Subtractor 60d may generally be operable to compare the filtered pressure measurement determined by filter 62d with a target pressure value (which may be set or selected by a user and/or by control system 44) to determine a filtered pressure error value, representing the difference between the target pressure value and the filtered pressure measurement. In some embodiments, subtractor 60d may output the difference between the target pressure value and the filtered pressure measurement if such difference is a positive value, and may output a value of zero (0) if the difference is a negative value.

Comparator 64d may generally be operable to compare the filtered pressure error value determined by subtractor 60d to a pressure error threshold and generate an output based on the comparison. In the depicted embodiment, comparator 64d may generate an output of TRUE or logic 1 if the filtered pressure error value is greater than the pressure error threshold, and may otherwise generate an output of FALSE or logic 0.

Filter 66d may generally be operable to filter a plurality of flow rate measurements detected over time by flow detector 40 to determine a filtered flow rate value. Comparator 68d may generally be operable to compare the filtered flow rate value determined by filter 66d to a first flow rate threshold value and generate an output based on the comparison. In the depicted embodiment, comparator 68d may generate an output of TRUE or logic 1 if the filtered flow rate value is less than the first flow rate threshold value, and may otherwise generate an output of FALSE or logic 0. Similarly, comparator 70d may generally be operable to compare the filtered flow rate value to a second flow rate threshold value (which may or may not be equal to the first flow rate threshold value) and generate an output based on the comparison. In the depicted embodiment, comparator 70d may generate an output of TRUE or logic 1 if the filtered flow rate value is greater than the second flow rate threshold value, and may otherwise generate an output of FALSE or logic 0.

AND gate 72d may generally be operable to output a first fault signal indicating whether or not a fault condition has been detected by fault detection system 46 by performing a logical AND of the outputs of comparators 64d and 68d. If the depicted embodiment, AND gate 72d generates an output of TRUE or logic 1 to denote a fault condition if each of comparators 64d and 68d generate an output of TRUE or logic 1; otherwise AND gate 72d generates an output of FALSE or logic 0 to denote no fault condition. Similarly, AND gate 74d may generally be operable to output a second fault signal indicating whether or not a fault condition has been detected by fault condition detection system 46 by performing a logical AND of the outputs of comparators 64d and 70d. In the depicted embodiment, AND gate 74d generates an output of TRUE or logic 1 to denote a fault condition if each of comparators 64d and 70d generate an output of TRUE or logic 1; otherwise AND gate 74d generates an output of FALSE or logic 0 to denote no fault condition.

In some embodiments, the generation of a fault signal by fault detection system 46 to denote a fault condition may indicate a fault associated with gas flow source 20. For example, in the embodiment depicted in FIG. 2, a fault condition generated by detecting a filtered pressure error value above the pressure error threshold value and detecting a filtered flow rate value below the first flow rate threshold value may indicate a malfunction or other fault associated with blower 21, e.g., that blower 21 has unexpectedly ceased to provide pressurized gas or has become stalled. As a further example, in the embodiment depicted in FIG. 2, a fault condition generated by detecting a filtered pressure error above the pressure error threshold value and detecting a filtered flow rate value greater than the second flow rate threshold value may be associated with a decoupling or disconnection of patient interface 24 from patient 30 or breathing assistance system 10, e.g., mask 28 becoming disengaged from the face and/or airway of patient 30.

In such situations, it may be desirable to alert a human of the fault condition and/or disable operation of the gas flow source 20 (e.g., blower 21) to prevent damage to breathing assistance system 10 or other deleterious effects, e.g., fire, injury to the patient, or undesired consumption of electrical power. Thus, in some embodiments, control system 44 may, in response to a determination by fault detection system 46 that a fault condition exists, cause breathing assistance system 10 to generate an alert detectable by a human. Such an alert may include, e.g., an audible alert generated by sound output device 52 or a visual alert displayed on user interface 50. In addition or alternatively, if fault detection system 46 determines that a fault condition exists, control system 44 may disable the operation of blower 21.

As noted above, in some embodiments, the target pressure value may be selected by a user of breathing assistance system 10, e.g., a patient or a caregiver. Such selection of the target pressure value can be made by means of any suitable system or device, for example, user interface 50. In some embodiments or situations, the target pressure value may be elected directly by a user, e.g., by using user interface 50. In other embodiments or situations, the target pressure value may be calculated by control system 44 based on one or more other parameters, e.g., gas flow parameters selected by a user or the selected ventilation mode (e.g., if a CPAP mode is selected, control system 44 may calculate the target pressure value based on experimentally determined optimum values for such mode; or a user may select a desired flow rate and control system 44 may calculate a target pressure value based at least on such desired flow rate).

In some embodiments, the first flow rate threshold value, the second flow rate threshold value and/or the pressure error threshold value are set to provide desired levels of sensitivity to the fault detection functionality disclosed herein. For example, first flow rate threshold value, second flow rate threshold value and/or the pressure error threshold may be set in order to minimize or eliminate determination of false positives or false negatives of fault conditions in breathing assistance system 10. In some embodiments, the first flow rate threshold value, the second flow rate threshold, value and/or the pressure error threshold value may be selected based on experimentation, e.g., experimentation by a manufacturer or a caregiver.

In some embodiments, at least one of the first flow rate threshold value, second flow rate threshold value and the pressure error threshold value may be selected by a user of breathing assistance system 10, e.g., a developer, manufacturer, or caregiver. Such selection of the first flow rate threshold value, second flow rate threshold value, and/or pressure error threshold value can be made by means of any suitable system or device, for example, user interface 50. In other embodiments, the first flow rate threshold value, second flow rate threshold value, and/or the pressure error threshold value may be automatically or otherwise determined based on the age, weight, tidal volume, respiratory rate, inhale sensitivity, exhale sensitivity, circuit leak, rise time, alarm settings, delay, ramp, starting pressure, inhalation:exhalation (I:E) ratio, capacity and/or other characteristics of the patient, a desired gas flow rate to the patient, desired gas pressure or pressures to the patient, a selected ventilation program, and/or various control (e.g., on/off control or algorithm selection) for the fault detection functionality, and may be automatically adjusted over time based on such parameters. In a particular embodiment, the pressure error threshold may be based at least on the target pressure value (e.g., the pressure error threshold may be automatically set or adjusted to some specified percentage of the target pressure value).

In some embodiments, the pressure error threshold value may range from about 1 cm $H_2O$ to about 3 cm $H_2O$. In a particular embodiment, the pressure error threshold may be about 2 cm $H_2O$. In some embodiments, the first flow rate threshold value may range from about 5 LPM to about 15 LPM. In a particular embodiment, the first flow rate threshold may be about 10 LPM. In some embodiments, the second flow rate threshold value may range from about 60 LPM to about 80 LPM. In a particular embodiment, the second flow rate threshold may be about 70 LPM.

In embodiments in which there are significant pressure fluctuations over time (e.g. during bi-level CPAP therapy), the embodiment depicted in FIG. 6A may be preferable over the embodiment depicted in FIG. 6B because of the pressure fluctuations associated with bi-level therapy.

Each of filters 62c, 62d, 66c and 66d may comprise any suitable system or device for filtering a plurality of values to reduce the effects of outlying values (e.g., pressure measurements, flow rate measurements, or pressure error values) or other transient faults associated with detecting pressure or flow rate in breathing assistance system 10, that might, without such filtering, cause false positives or false negatives of a fault condition. Such outlying measurements or transient faults may occur as a result of, e.g., a patient cough, the patient's natural breath cycle, or electromagnetic interference that may momentarily cause large transient pressure detection faults or low transient flow rate detection faults. Filters 62c, 62d, 66c and 66d may comprise, without limitation, one or more averagers and/or low-pass filters, such as infinite impulse response (IIR) filters, for example.

Each of subtractors 60c and 60d, filters 62c, 62d, 66c and 66d, comparators 64c, 64d, 68c, 68d, 70c and 70d, and AND gates 72c, 72d, 74c and 74d may comprise any suitable system or device for carrying out the functionality of each such component as discussed above. For example, in some embodiments each component of fault detection system 46 may be implemented on one or more integrated circuits, including without limitation a microcontroller, a digital signal processor (DSP), an application specific integrated controller (ASIC), electrically-programmable read-only memory (EPROM) or a field-programmable gate array (FPGA). In some embodiments, each of subtractors 60c and 60d, filters 62c, 62d, 66c and 66d, comparators 64c, 64d, 68c, 68d, 70c and 70d, and AND gates 72c, 72d, 74c and 74d may be contained on or within multiple integrated circuits. In another embodiment, two or more of subtractors 60c and 60d, filters 62c, 62d, 66c and 66d, comparators 64c, 64d, 68c, 68d, 70c and 70d, and AND gates 72c, 72d, 74c and 74d may be contained on the same integrated circuit.

In one embodiment, one or more of subtractors 60c and 60d, filters 62c, 62d, 66c and 66d, comparators 64c, 64d, 68c, 68d, 70c and 70d, and AND gates 72c, 72d, 74c and 74d may include software and/or executable code for analyzing input signals by the respective components to generate appropriate output signals as discussed above. In some embodiments, each of subtractors 60c and 60d, filters 62c, 62d, 66c and 66d, comparators 64c, 64d, 68c, 68d, 70c and 70d, and AND gates 72c, 72d, 74c and 74d may be implemented in different software programs or routines. In another embodiment, two or more of subtractors 60c and 60d, filters 62c, 62d, 66c and 66d, comparators 64c, 64d, 68c, 68d, 70c and 70d, and AND gates 72c, 72d, 74c and 74d may be implemented within the same software program or routine.

Figure 7A:
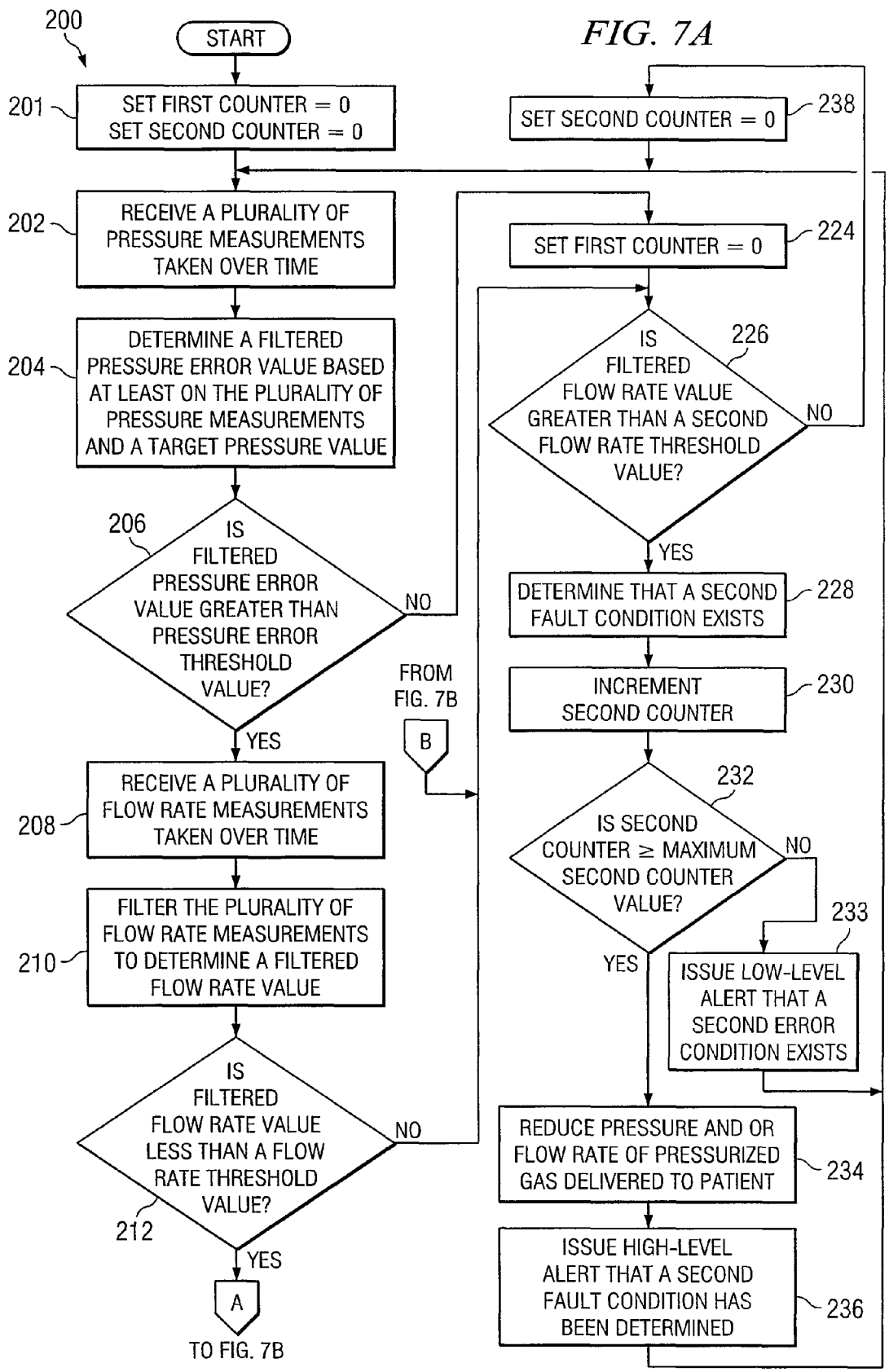
FIGS. 7A and 7B illustrate an example method of detecting a fault condition in the breathing assistance systems shown in FIGS. 1 and 2, in accordance with one embodiment of the disclosure.
Figure 7B:
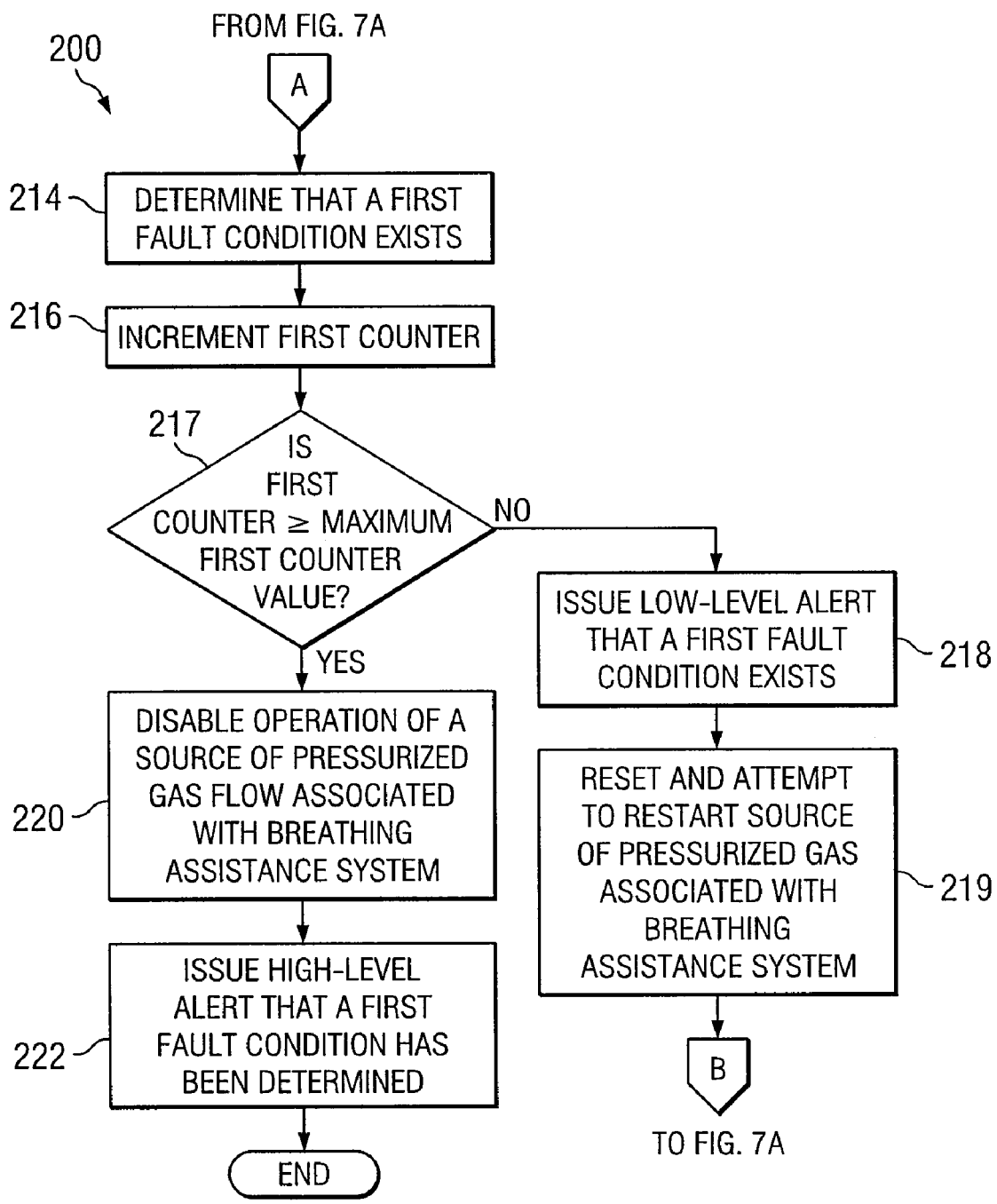

FIGS. 7A and 7B illustrate a method 200 of detecting a fault condition in a breathing assistance system, such as the breathing assistance systems 10 shown in FIG. 1 or 2, in accordance with one embodiment of the disclosure. FIGS. 8A and 8B each illustrate a method of determining a filtered pressure error value in method 200 shown in FIGS. 7A and 7B, in accordance with certain embodiments of the disclosure.

Turning to FIG. 7A, at step 201, each of a first counter and a second counter may be set to zero (0). Each counter may be implemented using any suitable method and/or system for implementing a counter. At step 202, fault detection system 46 may receive a plurality of pressure measurements taken over time by pressure detector 42. At step 204, fault detection system 46 may determine a filtered pressure error value based at least on the plurality of pressure measurements and a target pressure value.

In one embodiment of method 200, step 204 may be implemented by fault detection system 46 as shown in FIG. 8A. At step 204a, subtractor 60c of fault detection system 46 may compare each of the plurality of pressure measurements received from pressure detector 42 with the target pressure value to determine a plurality of pressure error values. Each determined pressure error value may be equal to the target pressure value minus a measured pressure from pressure detector 42. At step 204b, filter 62c of fault detection system 46 may filter the plurality of pressure error values to determine a filtered pressure error value.

In another embodiment of method 200, step 204 may be implemented by fault detection system 46 as shown in FIG. 8B. At step 204, filter 62d of fault detection system 46 may filter the plurality of pressure measurements received from pressure detector 42 to determine a filtered pressure measurement. At step 204, subtractor 60d may compare the filtered pressure measurement with the target pressure value to determine a filtered pressure error value. The filtered pressure error value may equal the target pressure value minus the filtered pressure measurement.

Referring again to FIG. 7A, at step 206, comparator 64c or 64d of fault detection system 46 may compare the filtered pressure error value with a pressure error threshold value. If the filtered pressure error value is not greater than the pressure error threshold value, method 200 may proceed to step 224. However, if the filtered pressure error value is greater than the pressure error threshold value, method 200 may proceed to step 208.

At step 208, fault detection system 46 may receive a plurality of flow rate measurements taken over time by flow rate detector 40. At step 210, filter 66c or 66d of fault detection system 46 may filter the plurality of flow rate measurements to determine a filtered flow rate value. At step 212, comparator 68c or 68d of fault detection system 46 may compare the filtered flow rate value with a first flow rate threshold value. If the filtered flow rate value is not less than the first flow rate threshold value, method 200 may proceed to step 226. However, if the filtered flow rate value is not greater than the first flow rate threshold value, method 200 may proceed to step 214 of FIG. 7B. At step 214, fault detection system 46 may, based at least on (a) the comparison of the filtered pressure error value to the pressure error threshold value at step 206, and (b) the comparison of the filtered flow rate value with the first flow rate threshold value at step 212, determine that a first fault condition exists.

At step 216, the first counter set to zero in step 201 may be incremented by one (1). Thus, the value of the counter at any given time may represent the number of consecutive instances that fault detection system 46, using method 200, has determined the existence of a first fault condition. At step 217, the value of the first counter may be compared against a first predetermined counter value threshold. If the first counter value is less than the first predetermined counter value threshold, method 200 may proceed to step 218 to issue an alarm, reset and attempt to restart gas flow source 20, and check whether the a second fault exists, as explained below. If the first counter value is greater than or equal to the first predetermined counter value threshold, method 200 may proceed to step 220 to disable the energy source of gas flow source 20, as explained below.

At step 218, control system 44, fault detection system 46, or another component of breathing assistance system 10 may cause sound output device 52 or user interface 50 to communicate an alert detectable to a human, e.g., an audible sound and/or a visual signal, in response to the determination of the fault condition at step 214. At step 219, control system 44, fault detection system 46, or another component of breathing assistance system 10 may reset and attempt to restart gas flow source 20. Method 200 may then proceed to step 226 of FIG. 7A to check whether a second fault condition exists.

At step 220, control system 44, fault detection system 46, or another component of breathing assistance system 10 may disable operation of gas flow source 20 (e.g., blower 21) in response to the determination at step 217 that the first counter value is greater than or equal to the first predetermined counter value threshold. At step 222, control system 44, fault detection system 46, or another component of breathing assistance system 10 may cause sound output device 52 or user interface 50 to communicate an alert detectable to a human, e.g., an audible sound and/or a visual signal, in response to the determination at step 217 that the first counter value is greater than or equal to the first predetermined counter value threshold. In some embodiments, the alert communicated at step 222 may be different than the alert communicated at step 218. In some embodiments, the alert communicated at step 222 may indicate that it is a higher-level alert or higher-priority alert than the alert communicated at step 218. Thus, control system 44, fault detection system 46, or another component of breathing assistance system 10 may disable operation of gas flow source 20 (e.g., blower 21) and/or communicate an alert if fault detection system 46 has determined a first fault to exist in a number of consecutive instances equal to the first predetermined counter value threshold. In some embodiments, the first predetermined counter value threshold may be set to provide desired levels of sensitivity to the fault detection functionality disclosed herein. For example, the first predetermined counter value threshold may be set in order to minimize or eliminate determination of false positives or false negatives of fault conditions in breathing assistance system 10. As another example, in situations in which the incidence of false positives or false negatives is not a concern, the first predetermined counter value threshold may be set to one (1), or the steps of method 200 relating to the first counter discussed above may be eliminated. In some embodiments the first predetermined counter value threshold may be selected based on experimentation, e.g., experimentation by a manufacturer or a caregiver.

After the execution of step 222, method 100 may end.

At step 224, the first counter value may again be set to zero (0), representing that method 200 determined that a first fault condition did not exist.

At step 226, comparator 70c or 70d of fault detection system 46 may compare the filtered flow rate value with a second flow rate threshold value. If the filtered flow rate value is not greater than the second flow rate threshold value, method 200 may proceed to step 238. However, if the filtered flow rate value is greater than the second flow rate threshold value, method 200 may proceed to step 228. At step 228, fault detection system 46 may, based at least on the comparison of (a) the filtered pressure error value to the pressure error threshold value at step 206, and (b) the comparison of the filtered flow rate value with the second flow rate threshold value at step 226, determine that a second fault has occurred.

At step 230, the second counter set to zero in step 201 may be incremented by one (1). Thus, the value of the counter at any given time may represent the number of consecutive instances that fault detection system 46, using method 200, has determined the existence of a second fault condition. At step 232, the value of the second counter may be compared against a second predetermined counter value threshold. If the first counter value is less than the second predetermined counter value threshold, method 200 may proceed to step 233 to issue an alarm and check whether the first fault exists or the second faults still exists, as explained below. If the second counter value is greater than or equal to the second predetermined counter value threshold, method 200 may proceed to step 234 to reduce the pressure and/or flow rate of gas delivered to patient 30, as explained below.

At step 233, control system 44, fault detection system 46, or another component of breathing assistance system 10 may cause sound output device 52 or user interface 50 to communicate an alert detectable to a human, e.g., an audible sound and/or a visual signal, in response to the determination of the second fault condition at step 228. Method 200 may return to step 202 check whether the first fault exists or the second faults still exists.

At step 234, control system 44, fault detection system 46, or another component of breathing assistance system 10 may reduce the pressure and/or flow rate of gas delivered to patient 30 in response to the determination at step 228 that the second counter value is greater than or equal to the second predetermined counter value threshold. At step 236, control system 44, fault detection system 46, or another component of breathing assistance system 10 may cause sound output device 52 or user interface 50 to communicate an alert detectable to a human, e.g., an audible sound and/or a visual signal, in response to the determination at step 228 that the second counter value is greater than or equal to the second predetermined counter value threshold. In some embodiments, the alert communicated at step 236 may be different than the alert communicated at step 233. In some embodiments, the alert communicated at step 236 may indicate that it is a higher-level alert or higher-priority alert than the alert communicated at step 233. Thus, control system 44, fault detection system 46, or another component of breathing assistance system 10 may disable operation of gas flow source 20 (e.g., blower 21) and/or communicate an alert if fault detection system 46 has determined a second fault to exist in a number of consecutive instances equal to the second predetermined counter value threshold. In some embodiments, the second predetermined counter value threshold may be set to provide desired levels of sensitivity to the fault detection functionality disclosed herein. For example, the second predetermined counter value threshold may be set in order to minimize or eliminate determination of false positives or false negatives of fault conditions in breathing assistance system 10. As another example, in situations in which the incidence of false positives or false negatives is not a concern, the second predetermined counter value threshold may be set to one (1), or the steps of method 200 relating to the second counter discussed above may be eliminated. In some embodiments the second predetermined counter value threshold may be selected based on experimentation, e.g., experimentation by a manufacturer or a caregiver.

At step 238, the first counter value may again be set to zero (0), representing that method 200 determined that a first fault condition did not exist. After execution of step 238, method 200 may return to step 202.

Although FIGS. 7A, 7B, 8A and 8B set forth a series of steps that may be utilized to determine the existence of a fault condition in breathing assistance device 10, it is understood that a fault condition may be detected without utilizing one or more of the steps described above or further utilizing one or more steps not described above. Furthermore, although FIGS. 7A, 7B, 8A and 8B set forth a particular order of steps that may be utilized to determine the existence of a fault condition in breathing assistance device 10, it is understood that a fault condition may be detected in accordance with the present disclosure using any order of steps discussed above.

Although the disclosed embodiments have been described in detail, it should be understood that various changes, substitutions and alterations can be made to the embodiments without departing from their spirit and scope.

What is claimed is:

1. A method of detecting a fault condition in a breathing assistance system for providing breathing assistance to a patient, the method performed by a control system configured to implement logic, instructions, and/or algorithms stored in computer readable storage media, the method comprising:
    the control system receiving from a pressure sensor a plurality of pressure measurements taken over time, each pressure measurement comprising a measurement of a gas pressure in the breathing assistance system;
    the control system determining a filtered pressure error value by comparing the plurality of pressure measurements to a target pressure value, the determination including filtering a plurality of values;
    the control system receiving from a flow sensor a plurality of flow rate measurements taken over time, each flow rate measurement comprising a measurement of a gas flow rate in the breathing assistance system;
    the control system filtering the plurality of flow rate measurements to determine a filtered flow rate value; and
    the control system comparing the filtered pressure error value to a pressure error threshold value;
    the control system determining the existence of a fault condition regarding the operation of the breathing assistance system, the fault condition determined based at least on both (a) the comparison of the filtered pressure error value to the pressure error threshold value and (b) the filtered flow rate value.

2. A method according to claim 1, wherein at least one of the filtering processes comprises an averaging process.

3. A method according to claim 1, wherein at least one of the filtering processes is performed using a low-pass filter.

4. A method according to claim 3, wherein at least one of the filtering processes is performed using an infinite impulse response (IIR) filter.

5. A method according to claim 1, wherein determining the filtered pressure error value comprises:
    filtering the plurality of pressure measurements to determine a filtered pressure measurement; and
    comparing the filtered pressure measurement with the target pressure value to determine the filtered pressure error value.

6. A method according to claim 5, wherein filtering the plurality of pressure measurements to determine a filtered pressure measurement comprises averaging the plurality of pressure measurements.

7. A method according to claim 5, wherein filtering the plurality of pressure measurements to determine a filtered pressure measurement comprises using a low-pass filter.

8. A method according to claim 1, wherein determining the filtered pressure error value comprises:
    comparing the plurality of pressure measurements with the target pressure value to determine a plurality of pressure error values; and
    filtering the plurality of pressure error values to determine the filtered pressure error value.

9. A method according to claim 8, wherein filtering the plurality of pressure error values to determine the filtered pressure error value comprises averaging the plurality of pressure error values.

10. A method according to claim 8, wherein filtering the plurality of pressure error values to determine the filtered pressure error value comprises using a low-pass filter.

11. A method according to claim 1, wherein determining the existence of a fault condition comprises:
    comparing the filtered pressure error value with a pressure error threshold value;
    comparing the filtered flow rate value with a flow rate threshold value; and
    determining the existence of a fault condition based at least on the results of the comparisons.

12. A method according to claim 11, wherein a fault condition is determined if (a) the filtered pressure error value is greater than the pressure error threshold value and (b) the filtered flow rate value is less than the flow rate threshold value.

13. A method according to claim 11, wherein at least one of the flow rate threshold value and the pressure error threshold value can be selected by a user.

14. A method according to claim 11, wherein at least one of the flow rate threshold value and the pressure error threshold value is automatically adjusted over time.

15. A method according to claim 11, wherein determining the existence of a fault condition comprises:
    determining number of instances in which (a) the filtered pressure error value is greater than the pressure error threshold value and (b) the filtered flow rate value is less than the flow rate threshold value;
    comparing the number of instances to a counter threshold value; and
    determining the existence of a fault condition based at least on the results of the comparison.

16. A method according to claim 1, further comprising communicating an alert detectable by a human if a fault condition is determined.

17. A method according to claim 1, further comprising disabling operation a source of pressurized gas flow associated with the breathing assistance system if a fault condition is determined.

18. A method according to claim 17, wherein the source of pressurized gas flow comprises a compressor.

19. A method according to claim 17, wherein the source of pressurized gas flow comprises a blower.

20. A method according to claim 1, wherein the source of pressurized gas flow comprises a wall gas source.

21. A method according to claim 1, wherein determining the existence of a fault condition comprises:
    comparing the filtered pressure error value with a pressure error threshold value;

comparing the filtered flow rate value with a first flow rate threshold value; and determining the existence of a first fault condition if (a) the filtered pressure error value is greater than the pressure error threshold value and (b) the filtered flow rate value is less than the first flow rate threshold value;

comparing the filtered flow rate value to a second flow rate threshold value; and determining the existence of a second fault condition if (a) the filtered pressure error value is greater than the pressure error threshold value and (b) the filtered flow rate value is greater than the second flow rate threshold value.

22. A method according to claim 21, wherein determining the existence of a fault condition further comprises:

comparing a first counter value threshold to the number of instances in which (a) the filtered pressure error value is greater than the pressure error threshold value and (b) the filtered flow rate value is less than the flow rate threshold value;

determining the existence of the first fault condition based at least on the results of the comparison of the number of instances in which (a) the filtered pressure error value is greater than the pressure error threshold value and (b) the filtered flow rate value is less than the flow rate threshold value;

comparing a second counter value threshold to the number of instances in which (a) the filtered pressure error value is greater than the pressure error threshold value and (b) the filtered flow rate value is greater than the second flow rate threshold value; and determining the existence of the second fault condition based at least on the results of the comparison of the number of instances in which (a) the filtered pressure error value is greater than the pressure error threshold value and (b) the filtered flow rate value is greater than the second flow rate threshold value.

23. A method according to claim 22, wherein the second fault condition is associated with a decoupling of a patient interface from a patient.

24. A method according to claim 1, wherein determining the existence of a fault condition comprises:

comparing the filtered pressure error value with a pressure error threshold value;

comparing the filtered flow rate value with a first flow rate threshold value;

comparing the filtered flow rate value with a second flow rate threshold value, the second flow rate threshold value being greater than the first flow rate threshold value; and determining the existence of a fault condition if (a) the filtered pressure error value is greater than the pressure error threshold value and (b) the filtered flow rate value is less than the first flow rate threshold value or greater than the second flow rate threshold value.

25. A method according to claim 1, wherein the breathing assistance system is adapted to provide at least one of continuous positive airway pressure (CPAP) and bi-level CPAP to a patient.

26. A method according to claim 1, wherein the breathing assistance system is adapted to provide ventilation support to a patient.

27. A method of detecting a fault condition in a breathing assistance system for providing breathing assistance to a patient and including a gas flow source, and a plurality of sensors including the pressure sensor and the flow sensor, the method performed by a control system configured to implement logic, instructions, and/or algorithms stored in computer readable storage media, the method comprising:

the control system receiving from a pressure sensor a plurality of pressure measurements taken over time, each pressure measurement comprising a measurement of a gas pressure in the breathing assistance system;

the control system determining a filtered pressure error value based at least on the plurality of pressure measurements and a target pressure value, the determination including filtering a plurality of values;

the control system receiving from a flow sensor a plurality of flow rate measurements taken over time, each flow rate measurement comprising a measurement of a gas flow rate in the breathing assistance system;

the control system filtering the plurality of flow rate measurements to determine a filtered flow rate value; and the control system determining the existence of a fault in the operation of the gas flow source based at least on both the filtered pressure error value and the filtered flow rate value.

28. A method according to claim 1, wherein: a fault in the operation of the gas flow source comprises a fault in the operation of a motor.

29. A method of detecting a fault condition in a breathing assistance system for providing breathing assistance to a patient, the method performed by a control system configured to implement logic, instructions, and/or algorithms stored in computer readable storage media, the method comprising:

the control system receiving from a pressure sensor a plurality of pressure measurements taken over time, each pressure measurement comprising a measurement of a gas pressure in the breathing assistance system;

the control system determining a filtered pressure error value based at least on the plurality of pressure measurements and a target pressure value, the determination including filtering a plurality of values;

the control system receiving from a flow sensor a plurality of flow rate measurements taken over time, each flow rate measurement comprising a measurement of a gas flow rate in the breathing assistance system;

the control system filtering the plurality of flow rate measurements to determine a filtered flow rate value;

the control system comparing the filtered pressure error value to a pressure error threshold value;

the control system comparing the filtered flow rate value to a flow rate threshold value;

the control system determining the existence of a fault condition regarding the operation of the breathing assistance system, including:

determining a fault condition to be present if both of the following are determined: (a) the filtered pressure error value is greater than the pressure error threshold value, and (b) the filtered flow rate value is less than the flow rate threshold value; and determining a fault condition not to be present if only one of the following is determined: (a) the filtered pressure error value is greater than the pressure error threshold value, and (b) the filtered flow rate value is less than the flow rate threshold value.

* * * * *